US011506659B2

(12) United States Patent
Hatamian et al.

(10) Patent No.: US 11,506,659 B2
(45) Date of Patent: *Nov. 22, 2022

(54) LATERAL FLOW ASSAY HOUSING WITH INTEGRATED SAMPLE AND BUFFER SOLUTION DELIVERY AND MEASUREMENT

(71) Applicants: Mehdi Hatamian, Mission Viejo, CA (US); Mehrtash Ghalebi, Irvine, CA (US)

(72) Inventors: Mehdi Hatamian, Mission Viejo, CA (US); Mehrtash Ghalebi, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/573,423

(22) Filed: Jan. 11, 2022

(65) Prior Publication Data

US 2022/0137043 A1     May 5, 2022

Related U.S. Application Data

(63) Continuation-in-part of application No. 17/353,230, filed on Jun. 21, 2021, now Pat. No. 11,229,906.

(Continued)

(51) Int. Cl.
*G01N 33/543* (2006.01)
*B01L 3/00* (2006.01)
*G01S 19/13* (2010.01)

(52) U.S. Cl.
CPC ...... *G01N 33/54388* (2021.08); *B01L 3/5023* (2013.01); *B01L 3/502715* (2013.01); *B01L 3/523* (2013.01); *G01S 19/13* (2013.01); *B01L 2300/023* (2013.01); *B01L 2300/069* (2013.01); *B01L 2300/0672* (2013.01); *B01L 2300/0835* (2013.01); *B01L 2400/0475* (2013.01); *B01L 2400/0683* (2013.01)

(58) Field of Classification Search
CPC ............ G01N 33/54388; B01L 3/5023; B01L 3/502715; B01L 3/523; B01L 2300/023; B01L 2300/0672; B01L 2300/069; B01L 2300/0835; B01L 2400/0475; B01L 2400/0683; B01L 2200/0605; B01L 2200/143; B01L 2300/021; B01L 2300/022; B01L 2300/044; B01L 2300/0825; B01L 2400/0406; G01S 19/13
See application file for complete search history.

(56) References Cited

U.S. PATENT DOCUMENTS

| | | | | |
|---|---|---|---|---|
| 11,229,906 B2* | 1/2022 | Hatamian | ............. | B01L 3/5023 |
| 2015/0346105 A1* | 12/2015 | Gutsell | ..................... | B01L 7/52 435/287.2 |

(Continued)

OTHER PUBLICATIONS

Portions of prosecution history of U.S. Appl. No. 17/353,230, dated Jan. 5, 2022, Hatamian, Mehdi, et al.

*Primary Examiner* — Dennis White
(74) *Attorney, Agent, or Firm* — Makoui Law, PC; Ali Makoui

(57) ABSTRACT

A lateral flow assay (LFA) device includes a capillary pad and a sample port that holds the sample fluid before a hole is made in a cavity surface of the sample port. The LFA device includes a breaker with a tip to make a hole in the cavity wall of the sample port causing the sample fluid held inside the compartment to be applied to the capillary pad after the start of a test.

19 Claims, 28 Drawing Sheets

Related U.S. Application Data

(60) Provisional application No. 63/083,988, filed on Sep. 27, 2020, provisional application No. 63/067,300, filed on Aug. 18, 2020, provisional application No. 63/041,973, filed on Jun. 21, 2020.

(56) References Cited

U.S. PATENT DOCUMENTS

2018/0339292 A1* 11/2018 Katz ................ G01N 33/54366
2021/0394174 A1   12/2021 Hatamian et al.

* cited by examiner

LATERAL FLOW ASSAY HOUSING WITH INTEGRATED SAMPLE AND BUFFER SOLUTION DELIVERY AND MEASUREMENT

CLAIM OF BENEFIT TO PRIOR APPLICATIONS

This application is a continuation-in-part of U.S. patent application Ser. No. 17/353,230, filed on Jun. 21, 2021, issued as U.S. Pat. No. 11,229,906. U.S. patent application Ser. No. 17/353,230 claims the benefit of U.S. Provisional Patent Application Ser. No. 63/041,973, filed on Jun. 21, 2020, U.S. Provisional Patent Application Ser. No. 63/067,300, filed on Aug. 18, 2020, and U.S. Provisional Patent Application Ser. No. 63/083,988, filed on Sep. 27, 2020. The contents of U.S. patent application Ser. No. 17/353,230, issued as U.S. Pat. No. 11,229,906, U.S. Provisional Patent Application 63/041,973, U.S. Provisional Patent Application Ser. No. 63/067,300, and U.S. Provisional Patent Application Ser. No. 63/083,988 are hereby incorporated by reference.

BACKGROUND

A Lateral flow assay (LFA), also referred to as lateral flow immunochromatographic assay or lateral flow dipstick immunoassay, is a device that is used to detect the presence (or absence) of a target analyte in a sample fluid without the need for specialized equipment. The lateral flow assays are widely used for medical diagnostics for point of care testing, home testing, or laboratory use.

A lateral flow assay typically includes a series of capillary pads for transporting fluid. A sandwich assay format may be used for detecting analytes that have at least two binding sites to bind to antibodies. A sample pad is used to receive a quantity of fluid (referred to as the sample fluid) and transport the sample fluid to an adjacent conjugate pad. The conjugate pad contains a solubilized antibody labeled with a detector such as colloidal gold nanoparticles. The antibody is specific to a certain analyte which is the target of interest in the sample fluid. Some lateral flow assays may not have a sample pad. In these assays, the sample may be directly applied to the conjugate pad. As the sample fluid flows through the conjugate pad, the analyte (if any) in the sample fluid binds with the labeled antibody on the conjugate pad and forms an immunocomplex.

The immunocomplex then flows from the conjugate pad into an adjacent membrane (or membrane pad). The membrane has one or more test lines. Each test line may contain an immobilized unlabeled antibody. As the immunocomplex moves over a test line, the immunocomplex binds with the immobilized antibody on the test line, resulting in a colored test line. When the sample fluid does not include the target analyte, no immunocomplex is formed on the conjugate pad and no immunocomplex binds with the immobilized antibody on the test line. As a result, the test line does not change color.

A lateral flow assay may also include a control line on the membrane. In a sandwich assay format, the control line may contain an immobilized antibody that binds to the free antibodies labeled with the detector resulting in a colored control line, which confirms that the test has operated correctly regardless of whether or not the target analyte has been present in the sample.

A competitive assay format may be used for detecting analytes that cannot simultaneously bind to two antibodies. The sample pad and the conjugate pad in a competitive assay format are similar to the sample pad and the conjugate pad in the sandwich assay format. In the competitive assay format, the test line contains immobilized analyte molecules.

If the sample liquid does not contain the analyte, the labeled antibody flows from the conjugate pad into the test line and binds to the analyte at the test line, resulting in a colored test line that indicates the lack of the target analyte in the sample liquid. If, on the other hand, the target analyte is present in the sample liquid, the analyte binds to the labeled antibodies on the conjugate pad and prevents the labeled antibody to bind to the analyte at the test line, resulting in the lack of color on the test line. In a competitive assay format, the control line may contain an immobilized analyte that binds to the free antibodies labeled with the detector resulting in a colored control line, which confirms that the test has operated correctly regardless of whether or not the target analyte has been present in the sample.

BRIEF DESCRIPTION OF THE DRAWINGS

The various embodiments of the present lateral flow assay housing with integrated sample and buffer solution delivery and measurement now will be discussed in detail with an emphasis on highlighting the advantageous features. These embodiments depict the novel and non-obvious lateral flow assay housing with integrated sample and buffer solution delivery and measurement shown in the accompanying drawings, which are for illustrative purposes only. These drawings include the following figures, in which like numerals indicate like parts.

DETAILED DESCRIPTION

Figure 1A:
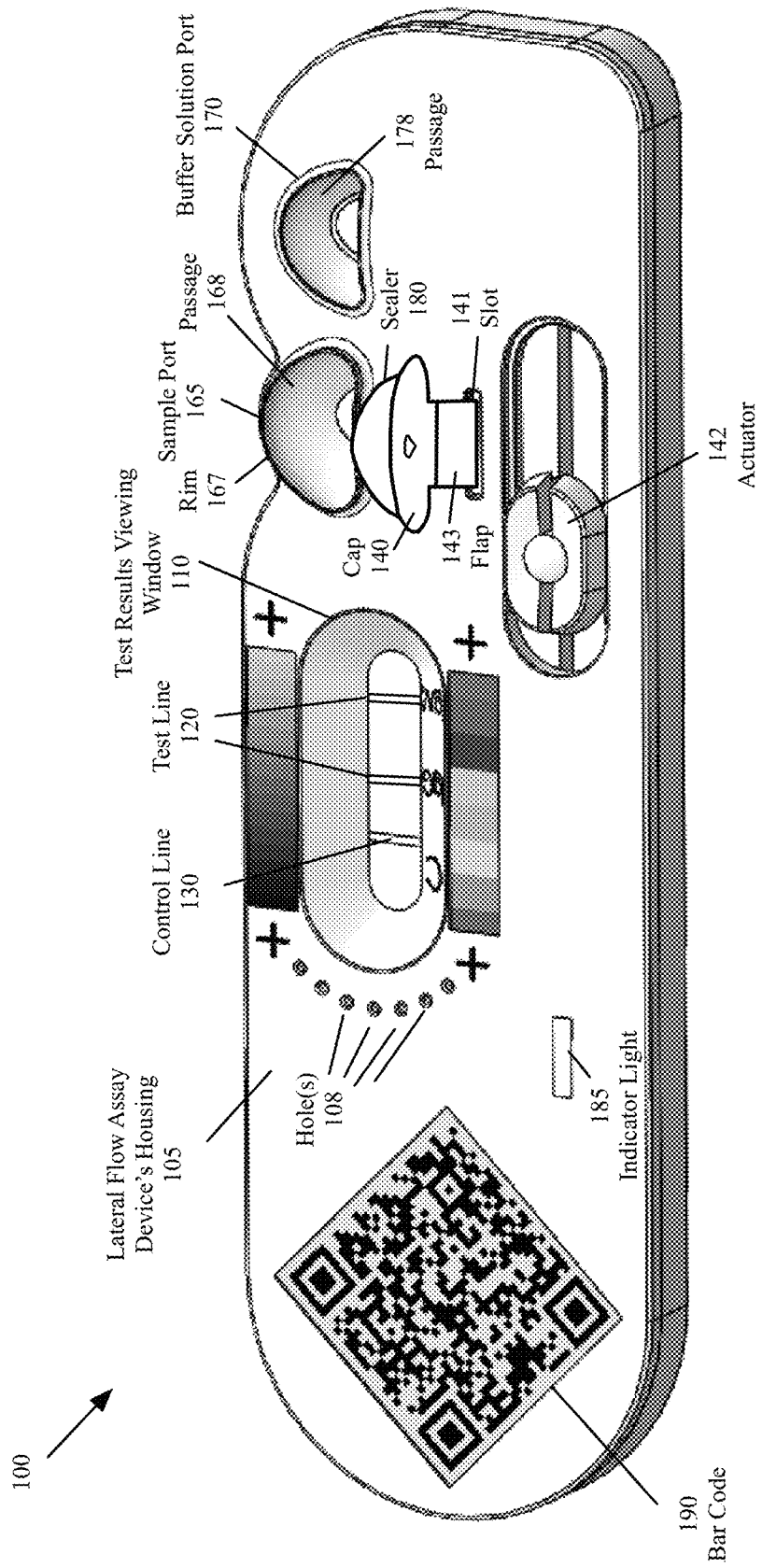
FIGS. 1A-1B illustrate top perspective views of an example lateral flow assay device with a cap and a sealer for applying a predetermined quantity of a sample through the sample port, according to various aspects of the present disclosure.

One aspect of the present embodiments includes the realization that, the previous lateral flow assay devices do not have a mechanism to control the amount of sample that is applied to the sample port. In the past, in order to apply a measured amount of sample fluid to a later flow assay device, laboratory tools such as pipettes were used. Disposable pipettes intended for use in home test kits are often difficult to use and lead to errors in obtaining the correct amount of sample which may result in errors in the outcome of the test. Since the lateral flow assay devices are optimized for a particular amount of sample, applying a different amount of sample may result in sub-optimal results, incorrect results, lack of consistency, etc.

The present embodiments, as described in detail below, solve the above-mentioned problem by providing a lateral flow assay device that includes an integrated mechanism for applying a predetermined quantity of sample fluid to the lateral flow assay device's capillary pads and prevents any excessive amounts of the sample fluid from being applied to the capillary pads. The lateral flow assay devices of present embodiments provide a single step method for applying a predetermined amount of sample, which provides the technical advantage of removing the sources of error, providing ease of use, and providing consistent results.

The lateral flow assay device, in some embodiments, may include a sample port and a buffer solution port. In some embodiments, the lateral flow assay device may include a quantity of buffer solution in the buffer solution port. For example, the buffer solution may be placed in the buffer port and the buffer port may be sealed at the manufacturing time.

The sample port and the buffer solution port may each include a passage through which the sample fluid or the buffer solution may be applied to the capillary pads, respectively. The passage may be a cavity with a surface. The cavity surface may include one or more walls. At least a portion of the cavity surface, in some embodiments, may be concave. At least a portion of the cavity surface of the sample port (e.g., a wall or a portion of a wall of the cavity surface) and/or a portion of the cavity surface of the buffer solution port (e.g., a wall or a portion of a wall of the cavity surface) may be made of a material that may be broken by pressing the breaker against the breakable portion of the surface. Both passages may be configured to hold the applied fluid inside prior to the start of the test and may prevent the sample and the buffer solution to be applied to the capillary pads until a hole is opened in the cavity surface of each port. The buffer solution port, in some embodiments, may be filled with a predetermined volume of the buffer solution during manufacturing and may be sealed at the top.

The lateral flow assay device, in some embodiments, may include a movable cap. Once the sample fluid is applied to the sample port, the cap may be closed. The cap, in some embodiments, may include a sealer that may be pushed inside the sample port and may snugly fit inside the sample port such that a compartment with a predetermined volume may be formed between the sealer and the sample port. The sealer may be configured such that pushing the sealer into the sample port may keep the sample inside the compartment and may push any extra amount of sample that does not fit inside the compartment out of the sample port.

The lateral flow assay device, in some embodiments, may include an actuator that may be connected to a breaker. The breaker may be configured to receive a force to press the breaker against the cavity surface of the sample port. In response to receiving the force, the breaker may make a hole in the cavity surface of the sample port, causing the sample fluid held by the sample port to be applied to the capillary pads.

The actuator, in some embodiments, may include a button. Depressing the actuator's button may cause the breaker to make a hole in the cavity surface of the sample port to allow the sample fluid inside the compartment to be applied to the capillary pads of the lateral flow assay device.

Depressing the actuator button may also cause the breaker to make a hole in the cavity surface of the buffer solution port in order to allow the buffer solution that is kept inside the buffer solution port to be applied to the capillary pads of the lateral flow assay device. The breaker, in some embodiments, may include tips for punching the holes in the cavity surface of the sample port and/or the buffer solution port.

In some embodiments, at least a portion of the cavity surface of the sample port (e.g., a wall or a portion of a wall of the cavity surface) may be configured to be thin and breakable and the hole may be made in the breakable portion of the cavity surface. In some embodiments, the cavity surface of the sample port (e.g., a wall of the cavity surface) may include a breakable tab and the hole may be made in the cavity surface of the sample port by breaking the tab. In some embodiments, at least a portion of the cavity surface of the buffer solution port (e.g., a wall or a portion of a wall of the cavity surface) may be configured to be thin and breakable and the hole may be made in the breakable portion of the cavity surface. In some embodiments, the cavity surface of the buffer solution port (e.g., a wall of the cavity surface) may include a breakable tab and the hole may be punched in the cavity surface of the buffer solution port by breaking the tab.

The actuator, in some embodiments, may include a slider that may be used to push the breaker's tips to make the holes in the cavity surface of the sample port and the buffer solution port. In other embodiments, the actuator may be a push-in button actuator that may be used to push the breaker towards the sample port and/or the buffer solution port in order for the breaker's tips to punch the hole in the cavity surface of the sample port and/or the cavity surface of the buffer solution port.

In other embodiments, the actuator may include a rotating handle, a cam, and a shaft. When the rotating handle is rotated, the cam may rotate around the shaft and may push the breaker towards the sample port in order for the breaker's tips to make the hole in the cavity surface of the sample port and/or the cavity surface of the buffer solution port.

Yet, in other embodiments, the actuator may be a button (e.g., a push button) that may be connected to the breaker. The breaker may include two tips at two sides of a shaft. The tips may rest on a guide surface. The breaker may be configured such that the portion of the breaker that includes the tips is elastic. As the actuator is pressed and the breaker is pushed against the guide, the tips may move away from the shaft and towards the cavity surface of the sample port and/or the cavity surface of the buffer solution port. The tips may then make the hole in the cavity surface of the sample port and/or the cavity surface of the buffer solution port.

The sealer, therefore, may ensure that only the amount of sample that has filled the predetermined volume of the compartment is applied to the capillary pads. The breaker may ensure that the holes are punched into the sample port and the buffer solutions port after the sample fluid is applied to the sample port. The breaker may further ensure that the sample and the buffer solutions are both applied to the capillary pads. The buffer solution delivered to the sample pad may have a predetermined volume that is filled in the buffer port and sealed during the manufacturing of the lateral flow assay cartridge. The predetermined amount is dependent on the test being performed by the lateral flow assay and is fixed for each type of test.

The lateral flow assay device's housing may be configured such that the sample port is located at an edge of the housing such that a portion of the sample port's rim is close to a side wall of the housing. When the sample fluid required for the test is blood, a person may punch a fingertip with a lancet and may simply and easily press the fingertip against the rim of the sample port to apply a quantity of blood to the sample port. The position of the rim on the side of the housing provides the technical advantage of allowing the blood to be applied from the fingertip to the sample port without spilling the blood on the lateral flow assay's housing. The rim and the position of the sample port may eliminate the need for using a pipette or other sampling devices to pick the blood from the finger and place it in the sample port.

The remaining detailed description describes the present embodiments with reference to the drawings. In the drawings, reference numbers label elements of the present embodiments. These reference numbers are reproduced below in connection with the discussion of the corresponding drawing features.

Figure 1B:
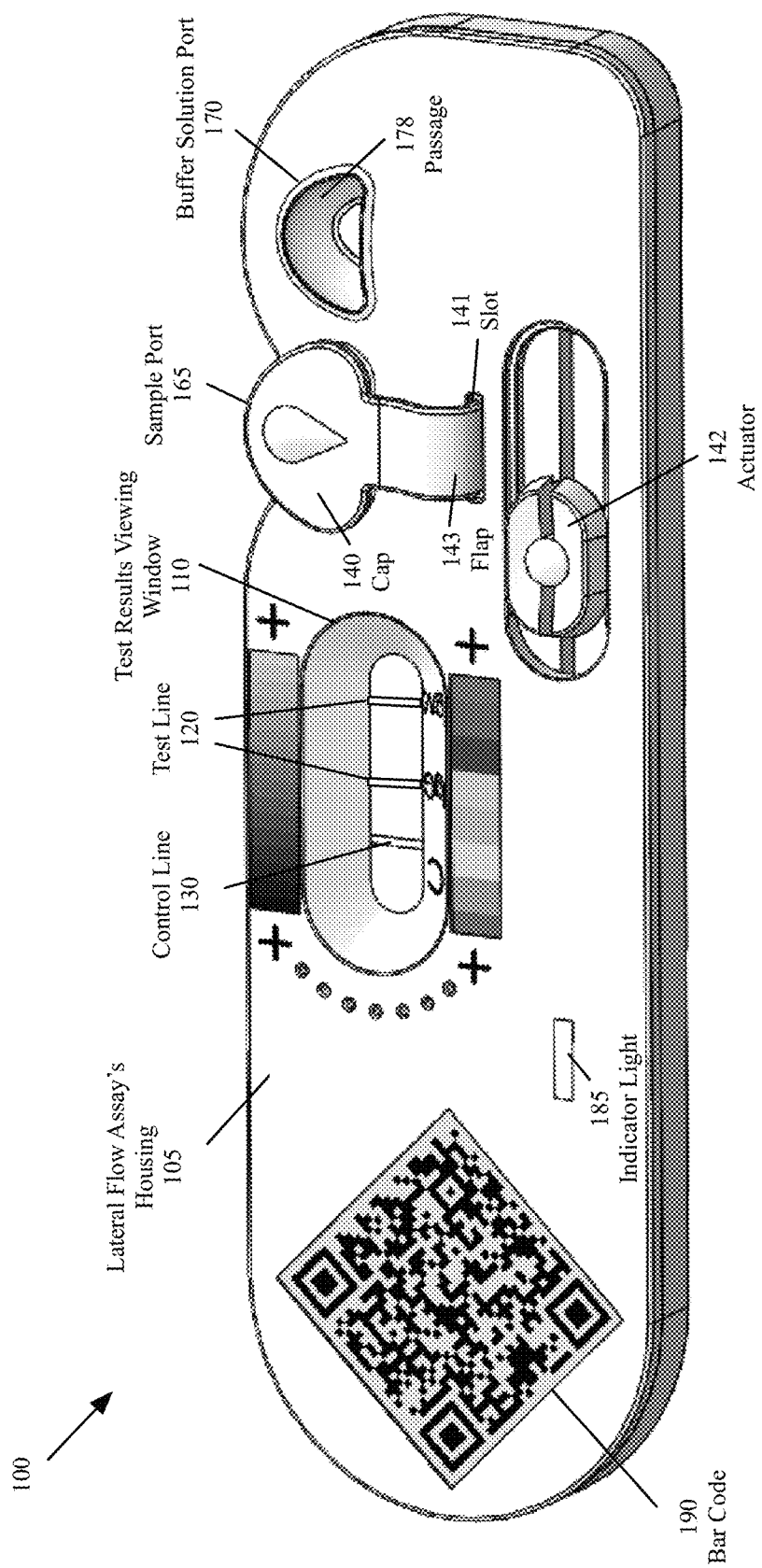

FIGS. 1A-1B illustrate top perspective views of an example lateral flow assay device with a cap and a sealer for applying a predetermined quantity of a sample fluid through the sample port, according to various aspects of the present disclosure. With reference to FIGS. 1A-1B, the lateral flow assay device 100 may include a housing 105, a test results viewing window 110, one or more test lines 120, a control line 130, a cap 140, an actuator 142, a sample port 165, a buffer solution port 170, and a sealer 180.

FIG. 1A shows the lateral flow assay device 100 with the cap 140 opened. FIG. 1B shows the lateral flow assay device 100 with the cap 140 closed, covering the sample port 165. For example, FIG. 1B may show the lateral flow assay device after a quantity of sample is applied to the sample port and the cap 140 is closed to start the test. The cap 140 may be connected to a flap 143 that may be rotate around the slot 141 in order to open or close the sample port 165.

When the sample fluid required for the test is blood, a person may punch a fingertip with a lancet and may simply and easily press the fingertip against the rim 167 of the sample port 165 to apply a quantity of blood to the sample port 165. The lateral flow assay device's housing 105, in some embodiments, may be configured such that the sample port 165 is located at an edge of the housing 105 such that a portion of the sample port's rim 167 is close to a side wall of the housing 105. In the pictured orientation, the sample port is located on the top, close to a wall of the housing 105 that is not shown in the perspective view of FIG. 1A. This wall 670 is shown, for example, in FIGS. 6, 9, and 13A-13B, described below. The position of the rim 167 on the side of the housing 105 provides the technical advantage of allowing the blood to be applied from the fingertip to the sample port 165 without spilling the blood on the lateral flow assay's housing 105.

The rim 167 and the position of the sample port 165 may eliminate the need for using a pipette or other sampling devices to pick the blood from the finger and place it in the sample port 165. Disposable pipettes intended for use in home test kits are often difficult to use and lead to errors in obtaining the correct amount of sample which can result in errors in the outcome of the test.

With further reference to FIG. 1A, the passage 168 may be a tube (which may be, e.g., and without limitations, at least partially funnel shaped). The buffer solution port 170 may include a passage 178. The passage 178 may be a tube (which may be, e.g., and without limitations, at least partially funnel shaped).

As described below, the passage 168 may be configured to hold the sample fluid until a hole is punched in the cavity surface of the sample port 165 in order for the sample fluid to be applied to the lateral flow assay device's capillary pads. The buffer solution passage 178 may be configured to hold the buffer solution until a hole is punched in the cavity surface of the passage 178 in order for the buffer solution to be applied to the lateral flow assay device's capillary pads.

In some embodiments, at least a portion of the cavity surface of the sample port (e.g., a portion of a wall) may be configured to be thin and breakable and the hole may be made in the breakable portion of the cavity surface. In some embodiments, the cavity surface of the sample port may include a breakable tab (e.g., on a wall of the cavity surface) and the hole may be made in the cavity surface of the sample port by breaking the tab. In some embodiments, at least a portion of the cavity surface of the buffer solution port (e.g., a portion of a wall) may be configured to be thin and breakable and the hole may be made in the breakable portion of the cavity surface. In some embodiments, the cavity surface of the buffer solution port may include a breakable tab (e.g., on a wall of the cavity surface) and the hole may be made in the cavity surface of the buffer solution port by breaking the tab. As described below, the actuator 142 may be connected to a breaker with tips that may make a hole and/or break a tab on the cavity surface of the ports 168 and/or 178 when the actuator is activated.

In some embodiments, the lateral flow assay device may include a quantity of buffer solution in the buffer solution port 170. For example, the buffer solution may be placed in the buffer solution port 170 and the buffer solution port 170 may be sealed at the manufacturing time. In other embodiments, the buffer solution may be applied to the buffer solution port 170 before the start of the test around the same time as a sample fluid is applied to the sample port 165. Yet other embodiments may perform a test that may not need a buffer solution. These embodiments may not include the buffer solution port or may include the buffer solution port but not use the buffer solution port for the test.

The sealer 180 on the cap 140 may be configured to snugly fit inside the sample port 165 such that a predetermined amount of sample fluid may be trapped inside the sample port's passage 168 and any additional amount of sample fluid may be blocked by the sealer 180 from reaching the lateral flow device's capillary pads.

The lateral flow assay device 100, in some embodiments, may include a bar code 190 and/or a near field communication (NFC) chip (not shown). The bar code 190, in some embodiments may be, for example, and without limitations, a one-dimensional (1D) barcode or a two-dimensional (2D) barcode. The bar code 190 and/or the NFC chip may identify the type (e.g., and without limitations, the model) of the lateral flow assay device, the type of test(s) to be performed by the lateral flow assay device, other parameters and information related to the test, etc. The bar code 190 and/or the NFC chip may also include a unique serial number used for authentication.

As described below with reference to FIGS. 6 and 7, the lateral flow assay device 100, in some embodiments, may include a timer that may be activated at the start of the test. The timer may turn an indicator light (e.g., and without limitations, a light emitting diode (LED)) 185 on or off to indicate the start and/or the end of the test. The lateral flow assay device's housing 105 may include one or more holes 108 that may facilitate the passage of an alert sound that may indicate the end of the test after the expiration of the timer.

Figure 2A:
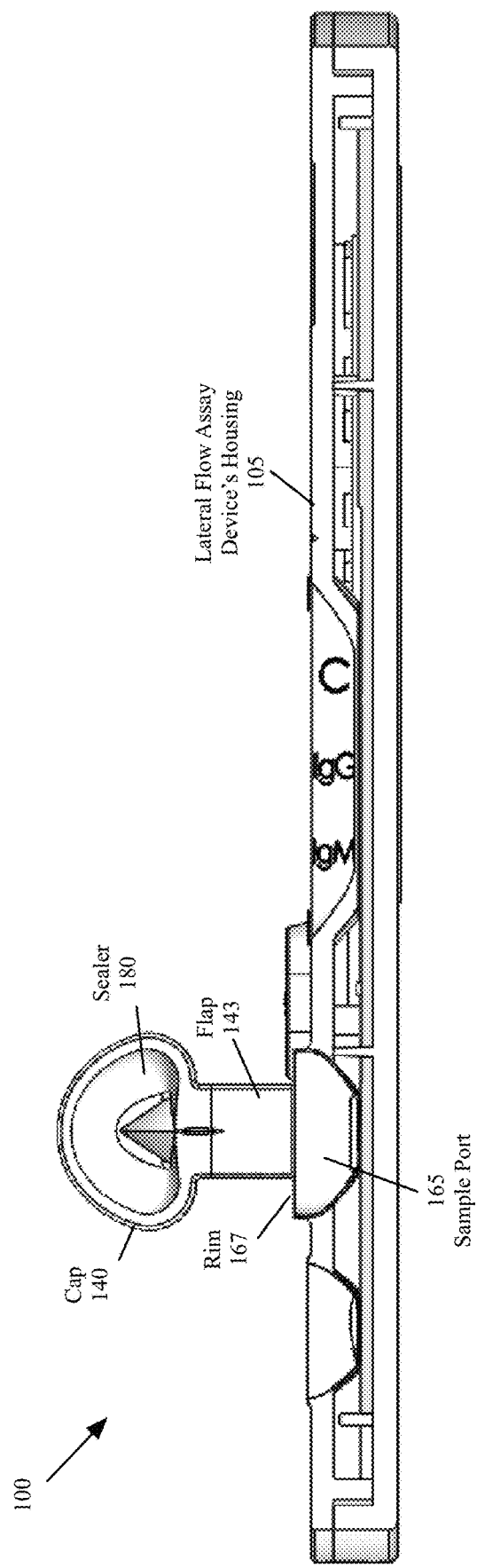
FIG. 2A illustrates a front elevation cross sectional view of the lateral assay device of FIGS. 1A-1B when the cap is open, according to various aspects of the present disclosure.
Figure 2B:
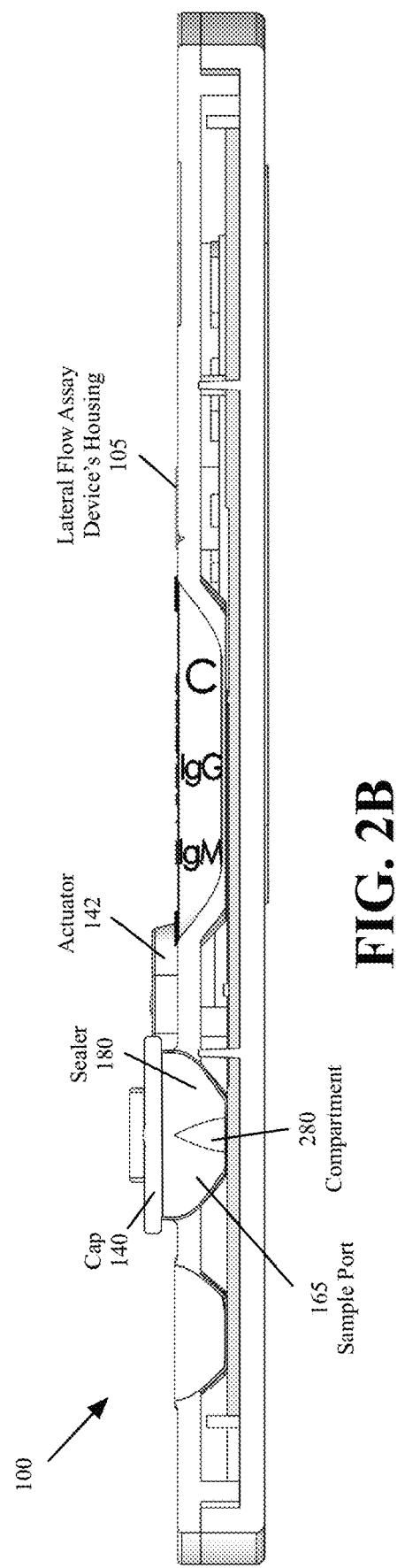
FIG. 2B illustrates a front elevation view of the lateral assay device of FIG. 2A when the cap is closed, according to various aspects of the present disclosure.

FIG. 2A illustrates a front elevation cross sectional view of the lateral assay device of FIGS. 1A-1B when the cap is open, according to various aspects of the present disclosure. FIG. 2B illustrates a front elevation view of the lateral assay device of FIG. 2A when the cap is closed, according to various aspects of the present disclosure.

With reference to FIGS. 2A-2B, when the cap 140 is closed, the sealer 180 may snuggly fit inside the sample port 165 such that a compartment 280 with a predetermined volume is formed inside the sample port between the sealer 180 and the cavity surface of the sample port 165. Depending on the type of the test performed by the lateral flow assay device 100, the shape and the size of the sample port 165, the shape of the cap 140, and the shape and the size of the sealer 180 are configured such that the compartment 280 may have a predetermined volume that may be required for the test, and may hold an amount of sample fluid that does not exceed the predetermined volume.

Any amount of the sample fluid that does not fit inside the compartment 280 may be pushed out of the sample port by the sealer 180. For example, in some embodiments, the extra sample fluid may be pushed over the sample port's rim 167 and may be kept under the cap 140. In some embodiments, the lateral flow assay device's housing 105 may include a groove (not shown) around the sample port 165 to hold the additional sample fluid that may be pushed out of the sample port by the sealer 180. The rim 167 may create an edge around the sample port 165 that is raised over the surface of the housing 105 and may prevent the additional sample fluid that is pushed out of the sample port 165 to return into the sample port's passage 168. Once the sample fluid is applied to the sample port 165 and the cap 140 is closed, the sample port's passage 168 may hold the sample until the actuator 142 is activated, as described below with reference to FIG. 3.

Figure 3:
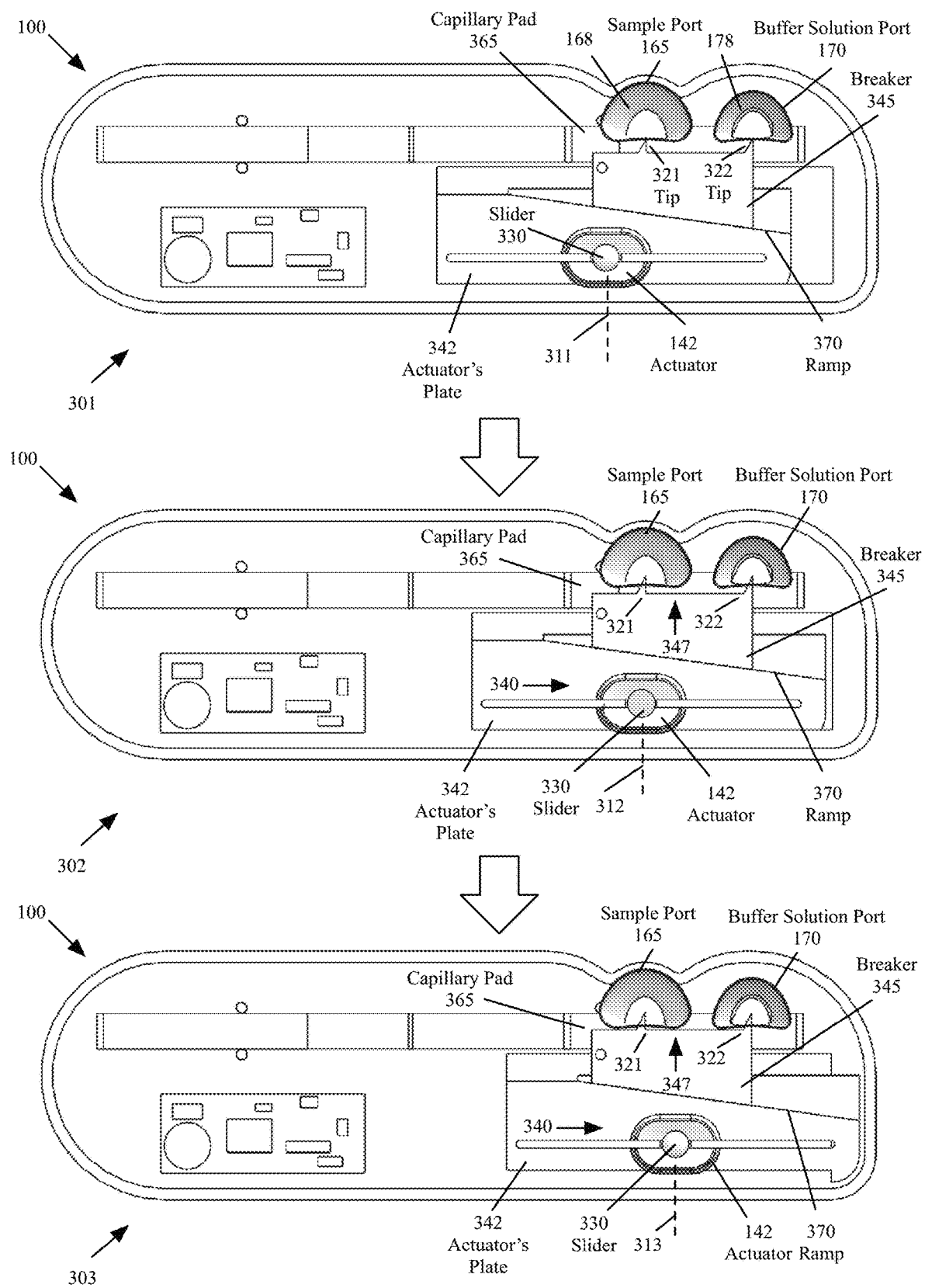
FIG. 3 is a top view of a cross sectional of the lateral flow assay of FIGS. 1A-1B, illustrating the operation of the actuator, according to various aspects of the present disclosure.

FIG. 3 is a top view of the cross section of the lateral flow assay of FIGS. 1A-1B, illustrating the operation of the actuator 142, according to various aspects of the present disclosure. With reference to FIG. 3, the actuator 142 may include a plate 342 and a slider 330. The breaker 345 may include the tips 321 and 322. One side of the actuator's plate 342 may include a ramp 370 configured to push the breaker 345 towards the sample port 165 and the buffer solution port 170 in order for the tips 321 and 322 of the breaker 345 to make holes on the cavity surfaces of the sample port 165 and the buffer solution port 170, respectively. In some embodiments, at least a portion of a cavity surface of the sample port and/or a portion of the cavity surface of the buffer solution port may be made from a material that may break when the tips 321 and 322 apply pressure to the breakable portion of the cavity surface. In other embodiments, the cavity surface of the sample port and/or the buffer solution port may include breakable tabs that may break when the tips 321 and 322 apply pressure to the tabs in the corresponding passages 168 and 178.

FIG. 3, as shown, includes three operational stages 301-303. In stage 301, the slider 330 that is connected to the actuator's plate 342 may be at position 311, which may be the left most position of the slider 330 in the pictured orientation. The breaker 345, in stage 301, is positioned on the ramp 370 such that the tips 321 and 322 may be close to, or may be touching, the exterior of the cavity surface of the sample port 165 and the exterior of the cavity surface of the buffer solution port 170, respectively. The tips 321 and 322, in stage 301, may not apply any pressure to break the cavity surfaces of the sample port 165 and the buffer solution port 170.

In stage 301, any sample fluid that is applied into the sample port 165 may be kept in the passage 168 without getting in contact with the capillary pad 365 of the lateral flow assay device 100. In the embodiments that include a sample pad, the capillary pad 365 may be the sample pad. In the embodiments that do not include a sample pad, the capillary pad 365 may be the conjugate pad. In the embodiments that include a plasma separator filter (red blood cell filter) the capillary pad 365 may be the filter pad.

In stage 302, the slider 330 may be moved in the direction of the arrow 340 from the position 311 to the position 312. The ramp 370 may push the breaker 345 towards the sample port 165 and the buffer solution port 170. In some embodiments, the breaker 345 may be configured to move on the direction of the arrow 347. For example, and without limitations, the lateral flow assay device 100, in some embodiments, may include stoppers and/or guides (not shown) around the breaker 345 to ensure the breaker 345 may move in the direction of the arrow 347 when the breaker 345 is pushed by the actuator's plate 342.

In stage 302, the tips 321 and 322 may apply pressure to the cavity surface of the sample port 165 and the cavity surface of the buffer solution port 170, respectively. As shown, the tips 321 and 322 may have punched a hole in the cavity surfaces of the sample port 165 and the buffer solution port 170, respectively.

The slider 330, in stage 303, may be moved further in the direction of the arrow 340 from the position 312 to the position 313. The ramp 370 may push the breaker 345 further towards the sample port 165 and the buffer solution port 170. The tip 321, in stage 303, may have made a hole in the cavity surface of the sample port 165 that may be enough to allow the sample liquid in the sample port 165 to be applied to the capillary pad 365. The tip 322, in stage 303, may have made a hole in the cavity surface of the buffer solution port 170 that may be enough to allow the buffer solution liquid in the buffer solution port 170 to be applied to the capillary pad 365.

It should be noted that, in some embodiments, the lateral flow assay device 100 may not include a buffer solution port. In these embodiments, the breaker 345 may not include the tip 322.

Figure 4:
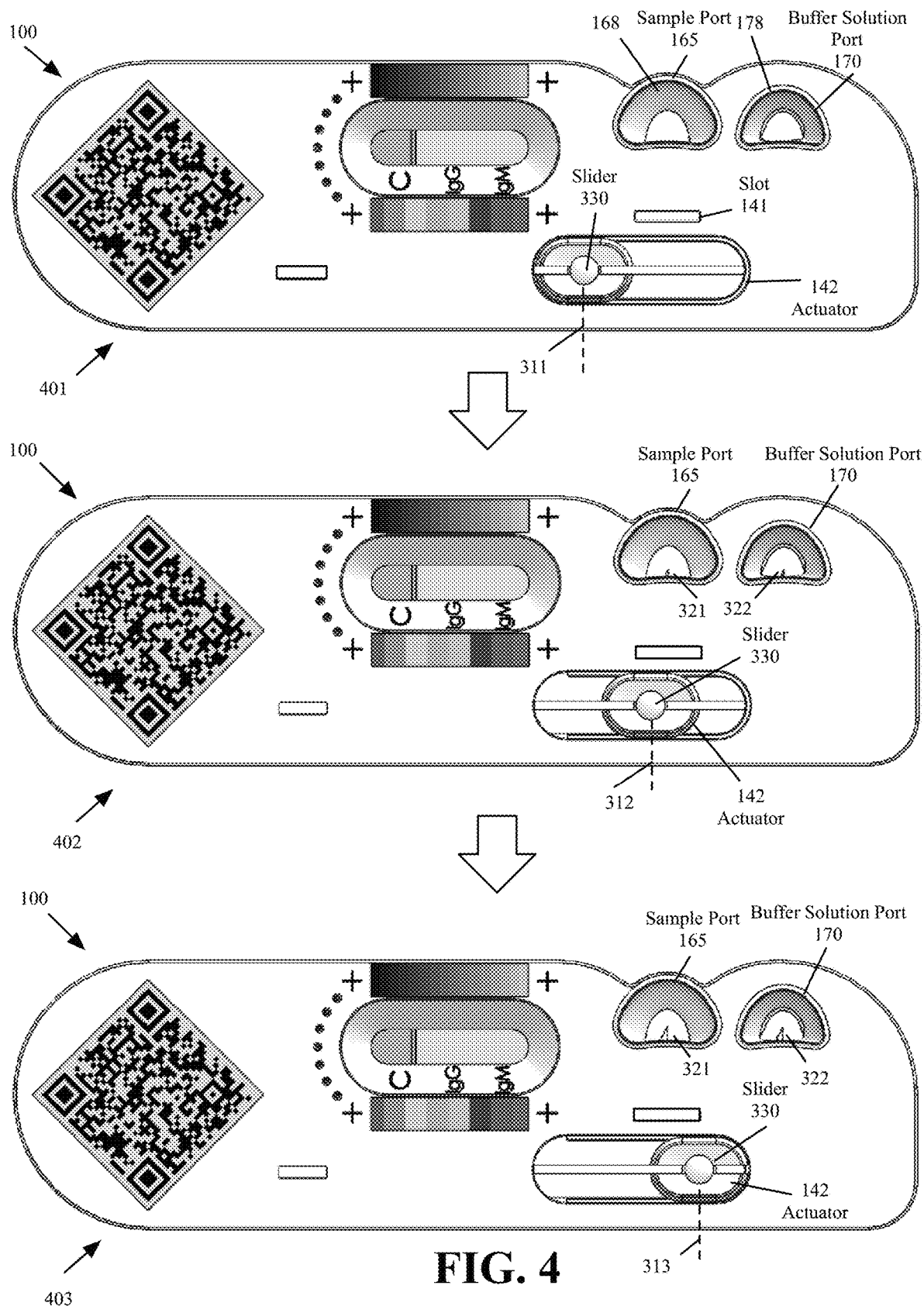
FIG. 4 is a top perspective view of the lateral flow assay of FIG. 3, illustrating the operation of the actuator, according to various aspects of the present disclosure.

FIG. 4 is a top perspective view of the lateral flow assay of FIG. 3, illustrating the operation of the actuator 142, according to various aspects of the present disclosure. FIG. 4, as shown, includes three operational stages 401-403, which correspond to the operational stages 301-303 of FIG. 3, respectively.

The cap 140, the flap 143, and the sealer 180 of FIG. 1A are not shown in FIG. 4 to provide a better view of the sample port 165 and the buffer solution port 170. In stage 401, the slider 330 may be at the position 311. The tips 321 and 322 are not visible in stage 401.

In stage 402, the slider 330 may have moved to the position 312. As shown, the tips 321 and 322 have penetrated into the passages 168 and 178, respectively. In stage 403, the slider 330 may have moved to the position 313. As shown, the tips 321 and 322 have further penetrated into the passages 168 and 178, respectively.

The tip 321, in stage 403, may have punched a hole in the cavity surface of the sample port 165 that may be enough to allow the sample liquid in the sample port 165 to be applied to the capillary pad 365 (FIG. 3). The tip 322, in stage 403, may have punched a hole in the cavity surface of the buffer solution port 170 that may be enough to allow the buffer solution liquid in the buffer solution port 170 to be applied to the capillary pad 365 (FIG. 3).

Figure 5:
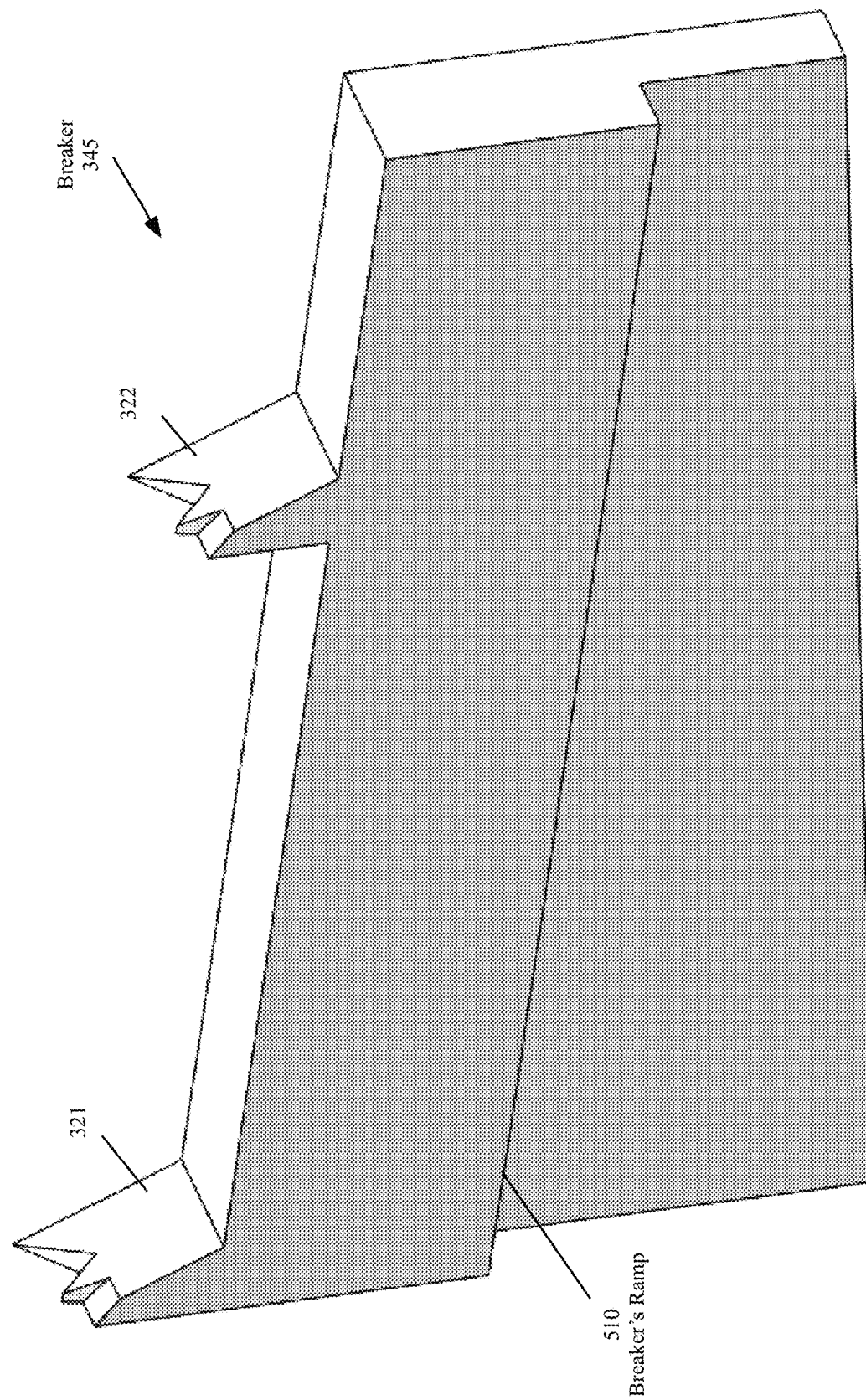
FIG. 5 is a top perspective view of an example breaker of a lateral flow assay device, according to various aspects of the present disclosure.

FIG. 5 is a top perspective view of an example breaker of a lateral flow assay device, according to various aspects of the present disclosure. As shown, the breaker 345 may include the tips 321 and 322. Although the lateral assay device 100 described above included a buffer solution port 170, some embodiments may not include a buffer solution port. In these embodiments, the breaker 345 may only include the tip 321. In some of these embodiments, depending on the type of test and the type of the sample, a buffer solution may not be needed or the buffer solution may be applied through the sample port prior to closing the cap 140 (FIG. 1A).

The breaker 345 may include a ramp 510. The breaker's ramp 510 and the actuator's ramp 370 (FIG. 3) may be configured be touch each other when the actuator slider is moved, causing the breaker 345 to move towards the sample port 165 and the buffer solution port 170, as described above with reference to FIG. 3.

The lateral flow assay device 100, in some embodiments may include electronic circuitry, such as, for example, and without limitations, a timer for generating one or more alert signals for indicating the start and/or the end of a test. FIG. 6 illustrates a top cross sectional view of an example lateral assay device with circuitry for generating one or more alert signals, according to various aspects of the present disclosure.

Figure 6:
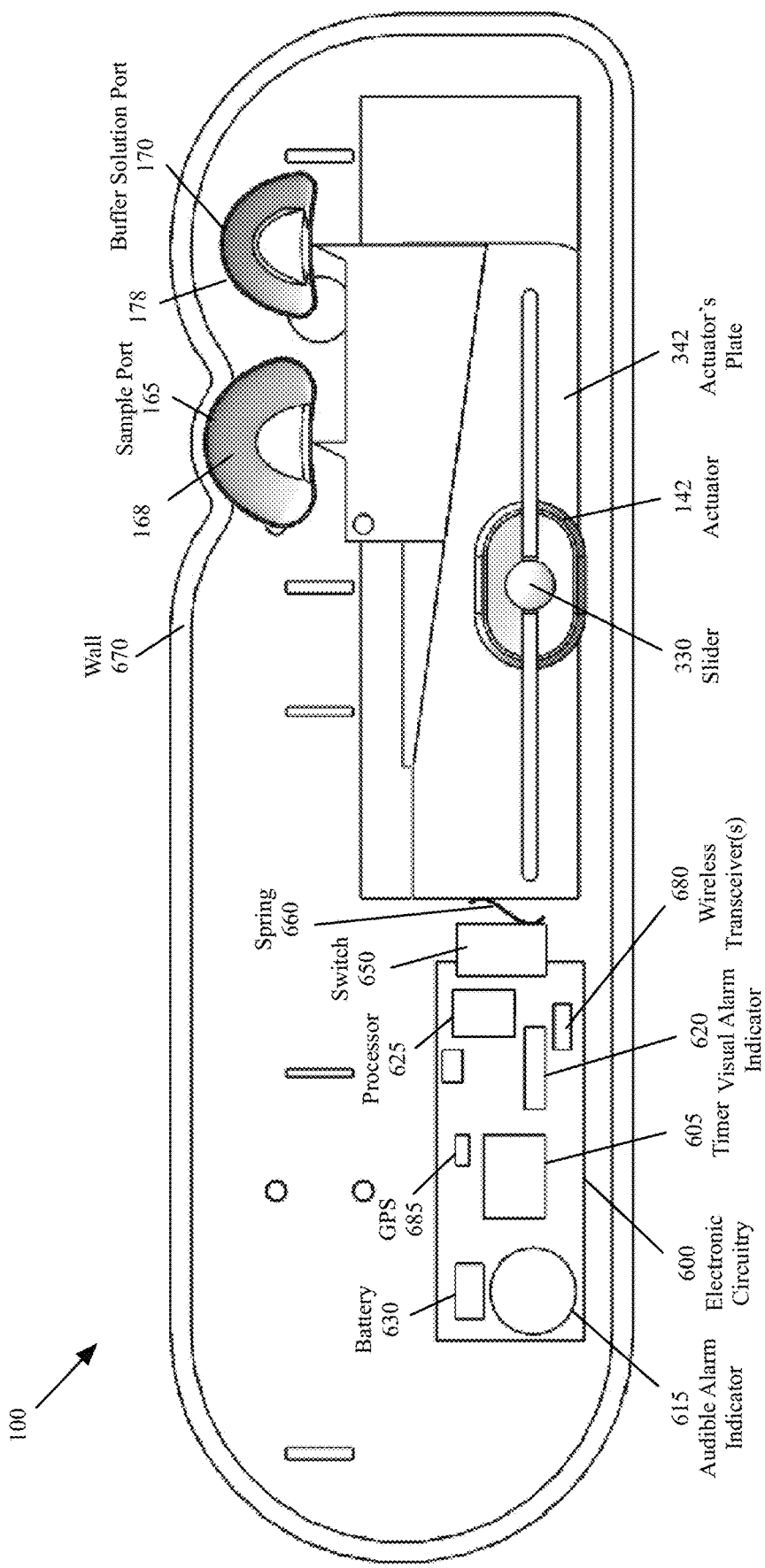
FIG. 6 illustrates a top cross sectional view of an example lateral assay device with circuitry for generating one or more alert signals, according to various aspects of the present disclosure.

With reference to FIG. 6, the lateral flow assay device 100 may include the electronic circuitry 600. The electronic circuitry 600, for example, and without limitations, may be on a circuit board, a printed board, a set of separate electronic chips, etc. The electronic circuitry 600, in some embodiments, may include a timer 605, an audible alarm indicator 615, a visual alarm indicator 620, a processor 625, one or more batteries 630, a switch 650, one or more wireless transceivers (e.g., and without limitations, to provide Bluetooth, Wi-Fi, etc., connectivity) 680, and/or a location determination module, such as, for example, and without limitations, a global positioning system (GPS) receiver 685. The electronic circuitry 600 may include additional components, such as, for example, and without limitations, capacitors, resistors, solenoids, buffers, etc.

With reference to FIG. 6, the lateral flow assay device 100 may include a spring 660. The spring 660 may be in touch with the actuator's plate 342 prior to the start of a test. For example, the lateral flow assay device 100, in some embodiments, may include a notch (not shown) that may hold the actuator's plate 342 in contact with the spring 660 prior to the start of the test. In these embodiments, the notch should be removed prior to the start of a test in order to move the slider 330 and the actuator's plate 342.

In some embodiments, the spring 660 may keep the switch 650 in a normally open state prior to the start of the test. The switch 650 may be, for example, and without limitations, a miniature snap-action switch, or a micro-switch, which is an electric switch that may be actuated by a small amount of physical force.

Figure 7:
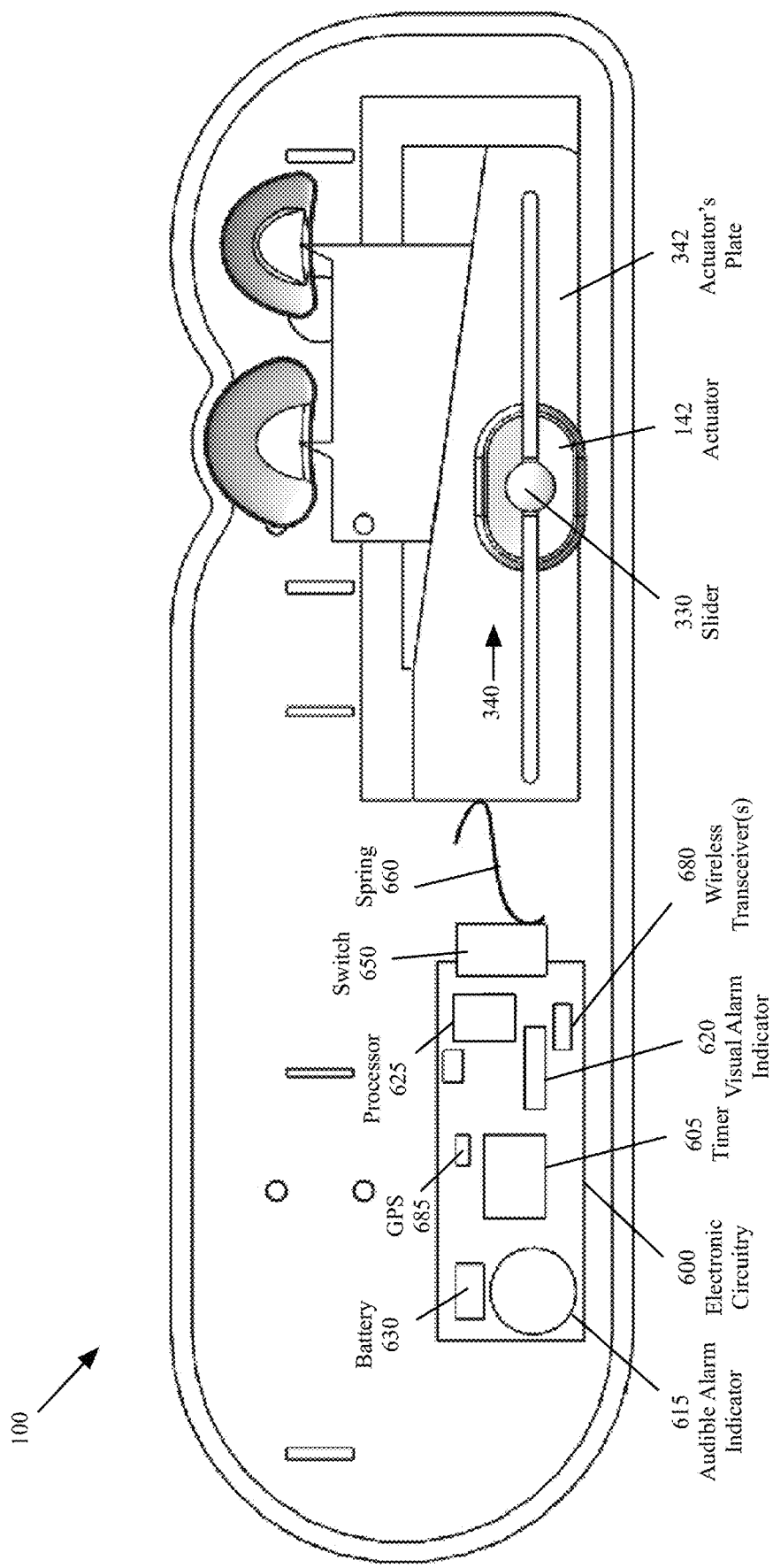
FIG. 7 illustrates a top cross sectional view of the lateral assay device of FIG. 6 after the spring actuates the switch, according to various aspects of the present disclosure.

FIG. 7 illustrates a top cross sectional view of the lateral assay device of FIG. 6 after the spring 660 actuates the switch 650, according to various aspects of the present disclosure. With reference to FIG. 7, the slider 330, the actuator 142, and the actuator's plate 342 may have moved in the direction of the arrow 340, away from the spring 660.

The spring 660 may be configured to close the switch when the actuator's plate 342 is in a position where the tips 321 and 322 have penetrated the passages 168 and 178. In some embodiments, closing the switch 600 may connect the battery (or batteries) 630 to other components of the electronic circuitry. In some embodiments, closing the switch 600 may start the timer 605. In other embodiments, after closing the switch 600, the processor 625 may start the timer 605.

The timer 605 may be pre-programmed, or may be programmed by the processor 625, to run for a time period that is required for the completion of the particular test for which the lateral flow assay device 100 is programmed. In some embodiments, once the timer 605 expires, the timer 605 may generate one or more signals to activate the audible alarm indicator 615 and/or the visual alarm indicator 620. In other embodiments, once the timer 605 expires, the timer 605 may send one or more signals to the processor 625. In response, the processor 625 may activate the audible alarm indicator 615 and/or may activate the visual alarm indicator 620. The lateral flow assay device's housing 105 may include one or more holes 108 (FIG. 1A) that may facilitate the passage of the visual alarm indicator's sound to the outside of the lateral flow assay device's housing 105. In some embodiments, a separate timer module may not be needed, in which case the processor itself may control the timing. In other embodiments, a processor may not be needed, in which case the timer chip itself may control the audio and visual alarms.

The audible alarm indicator 615 may be, for example, and without limitations, an audio signaling device such as a beeper or a buzzer. The audible alarm indicator 615 may be mechanical, electromechanical, or piezoelectric. The audible alarm indicator 615 may sound an audible alarm, indicating the end of the test when the test results may be ready for viewing.

The visual alarm indicator 620 may be, for example, and without limitations, a light source such as an LED light. The visual alarm indicator 620 may visually indicate the end of the test. For example, the visual alarm indicator 620 turn on at the end of the test, may start blinking at the start of the test and may stay on without blinking at the end of the test, etc.

The GPS receiver may receive the location of the lateral flow assay device from a group of satellite and may send the location to the processor. The processor may transmit the location of the lateral flow assay device to one or more authorized electronic devices through the wireless transceiver(s) and one or more networks. The location of the lateral flow assay device may be used by the authorized electronic device, for example, to collect statistics for geographical locations where a particular test is done by lateral flow assay devices.

It should be noted that part or all of the electronic circuitry 600, in some embodiments, may be optional. For example, some embodiments, may not include any of the electronic circuitry 600. Some embodiments may include all components of the electronic circuitry 600 (e.g., the timer 605, the audible alarm indicator 615, the visual alarm indicator 620, the processor 625, the one or more batteries 630, the switch 650, the one or more wireless transceivers 680, and the GPS receiver 680). Yet other embodiments may not include some components of the electronic circuitry 600 such as the GPS receiver 685, the wireless transceiver(s) 680, the timer 605 and the audible alarm, and/or the visual alarm indicator 620 while including other components of the electronic circuitry 600.

Figure 8:
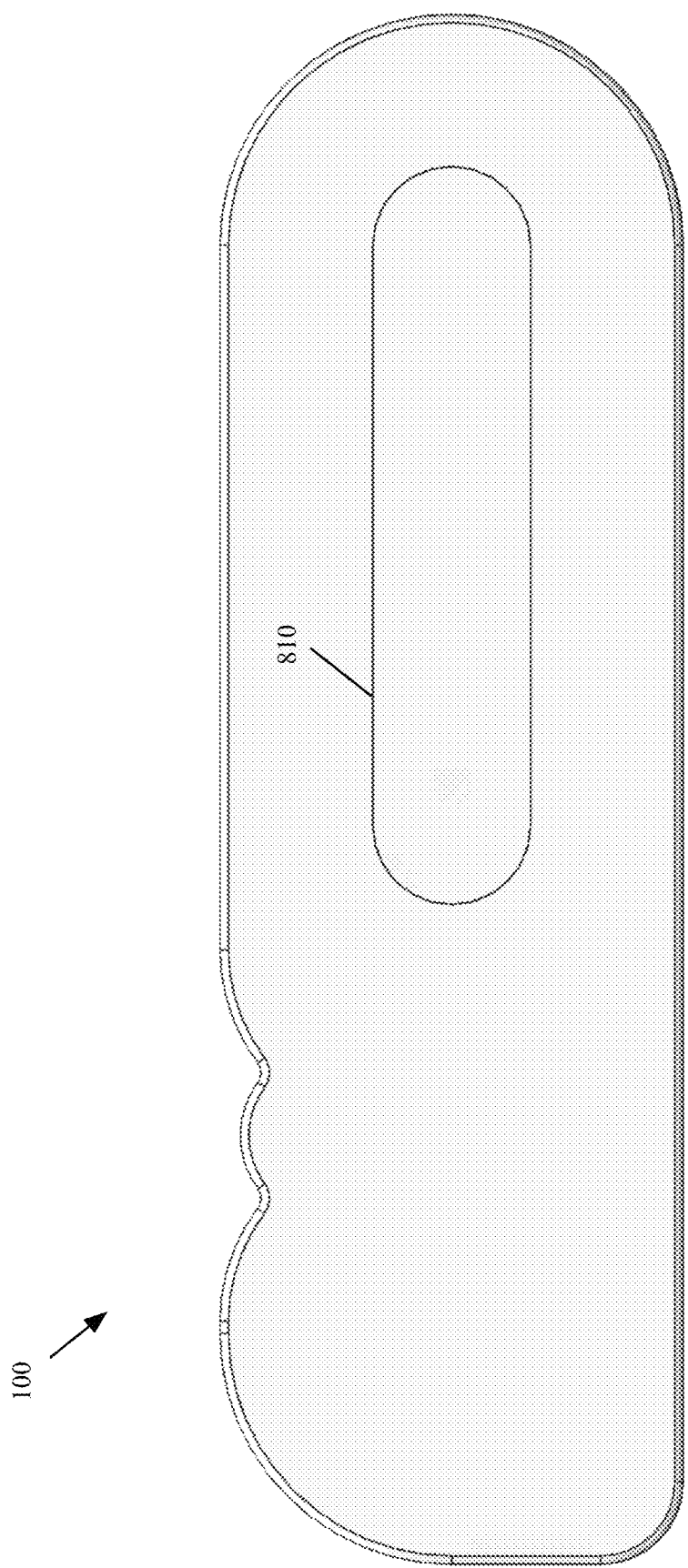
FIG. 8 illustrates a bottom view of an example lateral assay device, which includes a disinfecting pad, according to various aspects of the present disclosure.

The lateral flow assay device, in some embodiments, may include a disinfecting pad for disinfecting the fingertip of a person who is providing blood sample for the test. FIG. 8 illustrates a bottom view of an example lateral assay device 100, which includes a disinfecting pad, according to various aspects of the present disclosure.

With reference to FIG. 8, the lateral assay device 100 may include the disinfecting pad 810. The disinfecting pad 810, in some embodiments, may include an amount of disinfectant such as, for example, and without limitations, an amount of rubbing alcohol. The disinfecting pad 810 may be covered by a cover (not shown) that may keep the disinfecting pad 810 wet and may be peeled off in order to disinfect the finger of a person. It should be understood that, in different embodiments, the size, the shape, and the location of the disinfecting pad 810 may be different.

Figure 9:
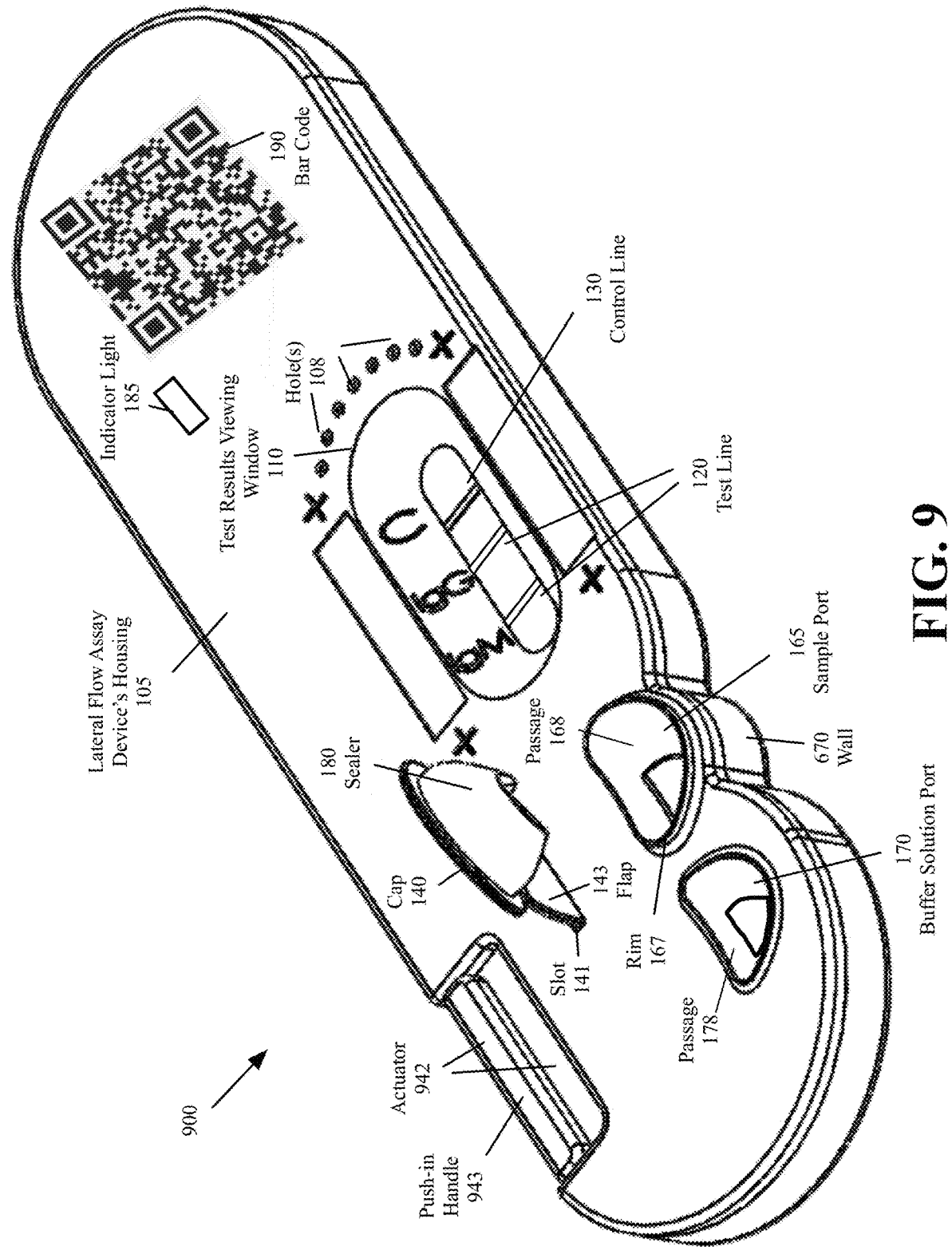
FIG. 9 illustrates a top perspective view of an example lateral flow assay device with a push-in actuator, according to various aspects of the present disclosure.

The actuator in the embodiments described with reference to FIGS. 1A-7 included a slider. In some embodiments, the actuator may include a push-in handle that may be used to push the breaker's tips to make a hole in the cavity surface of the sample port and/or the cavity surface of the buffer solution port. FIG. 9 illustrates a top perspective view of an example lateral flow assay device with an actuator that includes a push-in handle, according to various aspects of the present disclosure.

With reference to FIG. 9, the lateral flow assay device 900 may include a housing 105, one or more holes 108, a test results viewing window 110, one or more test lines 120, a control line 130, a cap 140, a slot 141, a flap 143, a sample port 165, a rim 167, a buffer solution port 170, passages 168 and 178, a sealer 180, an indicator light 185, a bar code 190, an/or an NFC chip (not shown), which may be similar to the corresponding components of FIGS. 1A-1B. The lateral flow assay device 900 may include an actuator 942, which may include a push-in handle (or button) 943. The lateral flow assay device 900 may include capillary pads such as sample pad, conjugate pad, membrane, wicking pad, and/or filter pad.

Similar to the lateral flow assay device 100 of FIGS. 6 and 7, the lateral flow assay device 900 may include some or all of the electronic circuitry 600, such as, a timer 605, an audible alarm indicator 615, a visual alarm indicator 620, a processor 625, one or more batteries 630, a switch 650, one or more wireless transceivers 680, and/or a GPS receiver 685. The electronic circuitry may include additional components, such as, for example, and without limitations, capacitors, resistors, solenoids, buffers, etc. The lateral flow assay device 900 may also include a spring 660, similar to the spring 660 of FIG. 6.

The electronic circuitry may include additional components, such as, for example, and without limitations, capacitors, resistors, solenoids, buffers, etc. The sample port 165 of the lateral flow assay device 900 may be close to an edge of the lateral flow assay device 900, for example close to the wall 670 to facilitate applying blood sample to the sample port 165.

Figure 10:
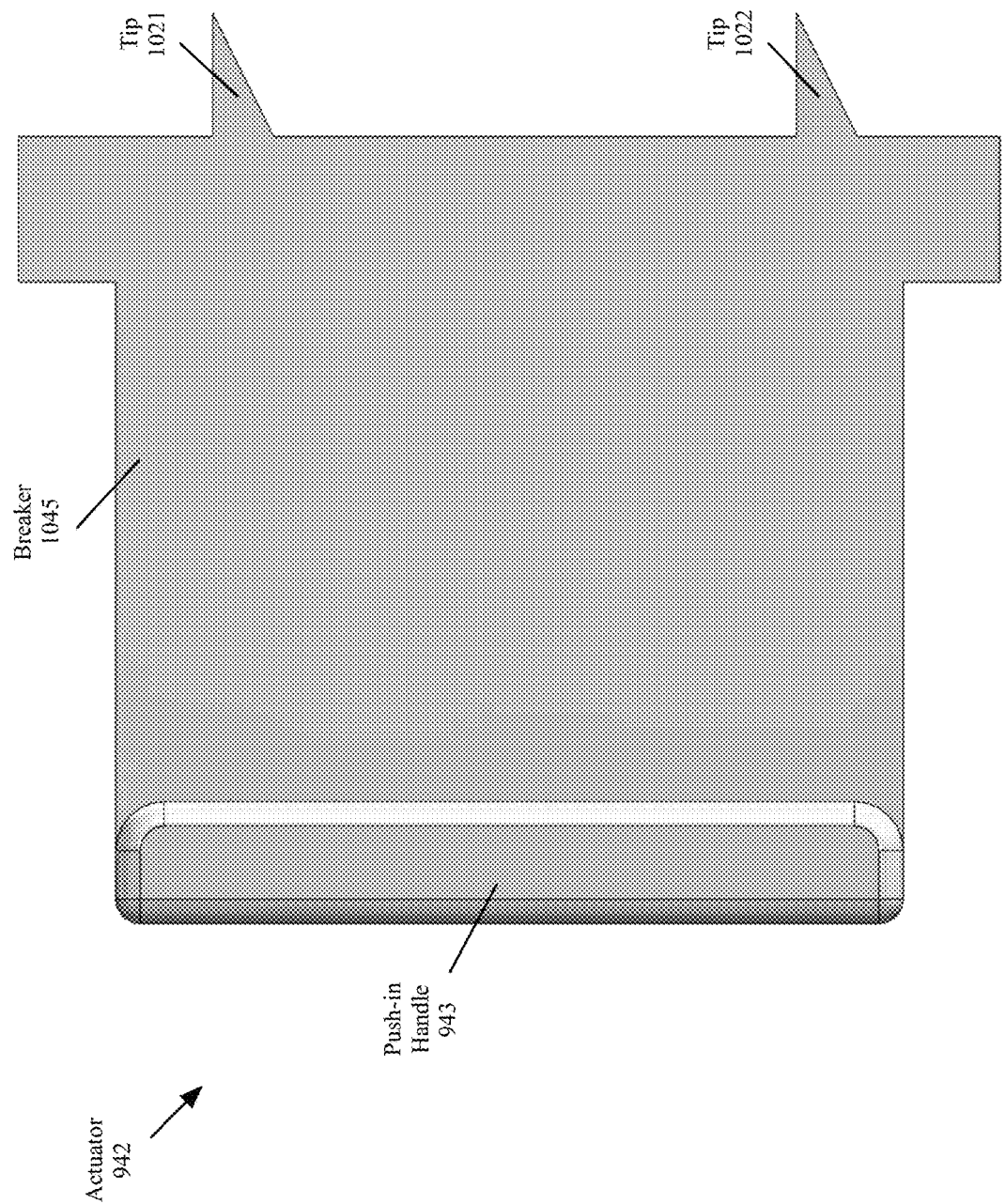
FIG. 10 illustrates a top view of an example push-in actuator of a lateral flow assay device, according to various aspects of the present disclosure.
Figure 11:
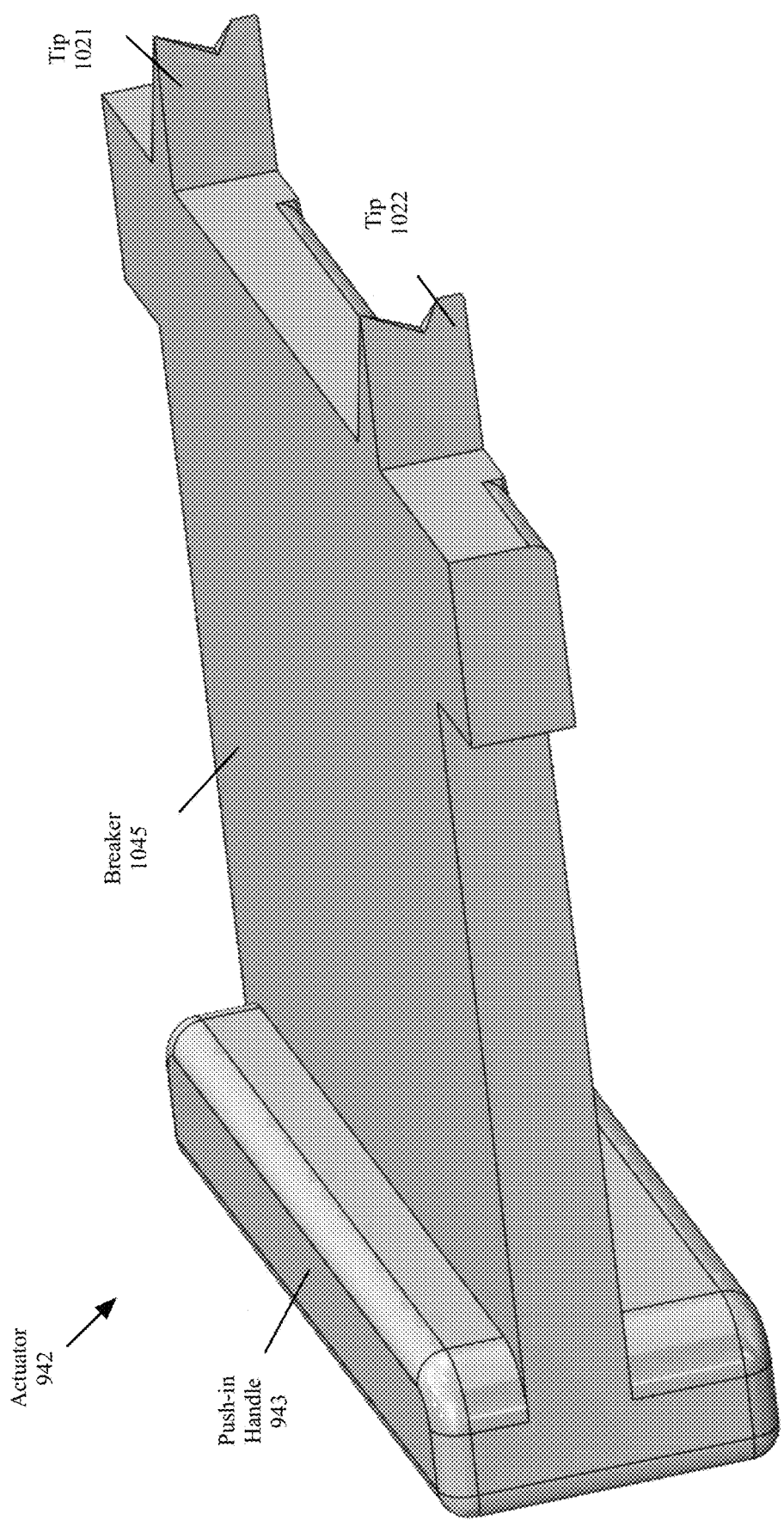
FIG. 11 illustrates a side perspective view of the push-in actuator of FIG. 10, according to various aspects of the present disclosure.

FIG. 10 illustrates a top view of an example actuator with a push-in handle of a lateral flow assay device, according to various aspects of the present disclosure. FIG. 11 illustrates a side perspective view of the actuator of FIG. 10, according to various aspects of the present disclosure. With reference to FIGS. 10 and 11, the actuator 942 may include, and/or may be attached to, a breaker 1045. The breaker 1045 may include the tips 1021 and 1022.

Although the lateral assay device 900 described above included a buffer solution port 170, some embodiments may not include a buffer solution port. In these embodiments, the breaker 1045 may only include the tip 1021. In some of these embodiments, depending on the type of test and the type of the sample, a buffer solution may not be needed or the buffer solution may be applied through the sample port prior to closing the cap 140 (FIG. 9).

Figure 12:
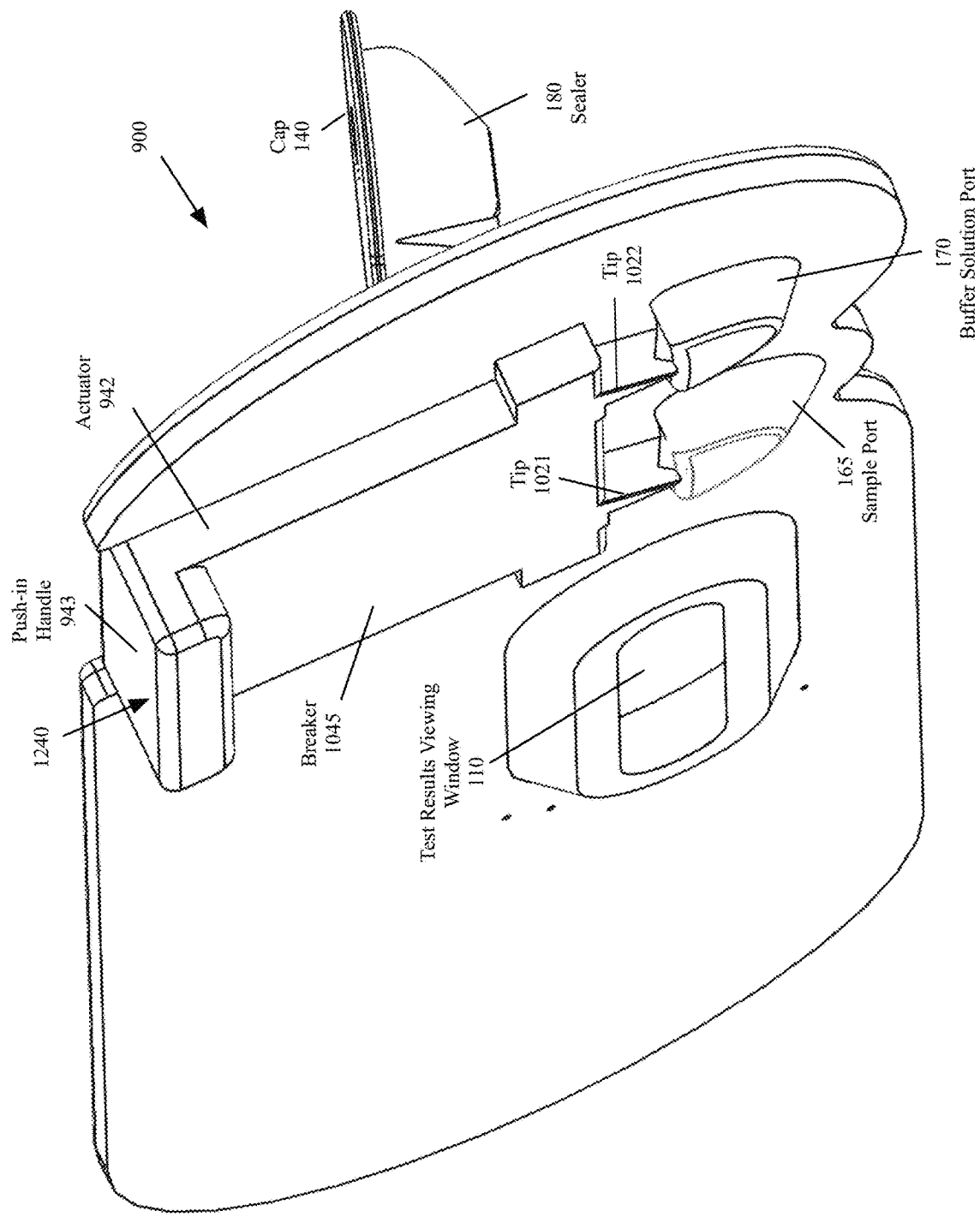
FIG. 12 illustrates a bottom cross sectional view of the lateral assay device of FIG. 9, according to various aspects of the present disclosure.

FIG. 12 illustrates a bottom cross sectional view of the lateral assay device of FIG. 9, according to various aspects of the present disclosure. With reference to FIG. 12, the actuator 942 may include the push-in handle (or push-in button) 943. The actuator 942 may include, and/or may be connected to, the breaker 1045.

When the push-in handle 943 is pushed towards the sample port 165 (in the direction of the arrow 1240), the tip 1021 may make a hole in the cavity surface of the sample port 165 that may be enough to allow the sample liquid in the sample port 165 to be applied to the capillary pad (not shown in the cross section of FIG. 12) located below the sample port. When the push-in handle 943 is pushed in the direction of the arrow 1240, the tip 1022, may make a hole in the cavity surface of the buffer solution port 170 that may be enough to allow the buffer solution liquid in the buffer solution port 170 to be applied to the capillary pad (not shown) located below the buffer solution port 170.

In some embodiments, at least a portion of the cavity surface of the sample port (e.g., a portion of a wall of the cavity surface) and/or a portion of the cavity surface of the buffer solution port (e.g., a portion of a wall of the cavity surface) may be made from a material that may break when the tips 1021 and 1022 apply pressure to the breakable portions of the walls. In other embodiments, the cavity surface of the sample port (e.g., a wall of the cavity surface) and/or the cavity surface of the buffer solution port (e.g., a wall of the cavity surface) may include breakable tabs that may break when the tips 1021 and 1022 apply pressure to the corresponding tabs.

In embodiments described with reference to FIGS. 1A-7, the actuator included a slider and, in the embodiments described with reference to FIGS. 9-12, the actuator included a push-in handle (or button). The actuator, in some embodiments, may include a handle that may make a circular motion and may be connected to a cam that moves the breaker forward to make the breaker's tips make holes in the cavity surfaces of the sample port and the buffer solution port.

Figure 13A:
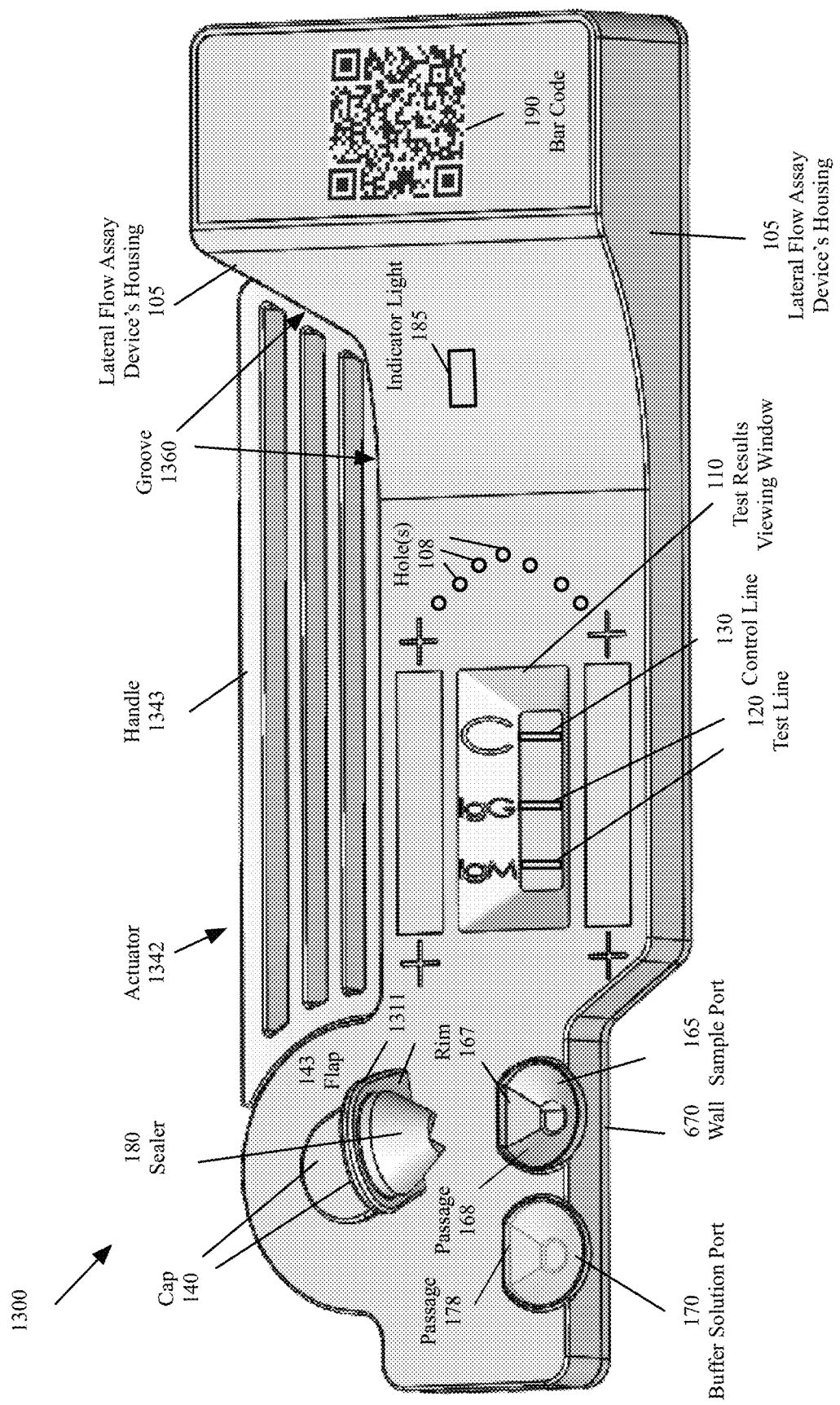
FIGS. 13A-13B illustrate top perspective views of an example lateral flow assay device with a cap and a sealer for applying a predetermined quantity of a sample through the sample port and an actuator with a rotating handle, according to various aspects of the present disclosure.
Figure 13B:
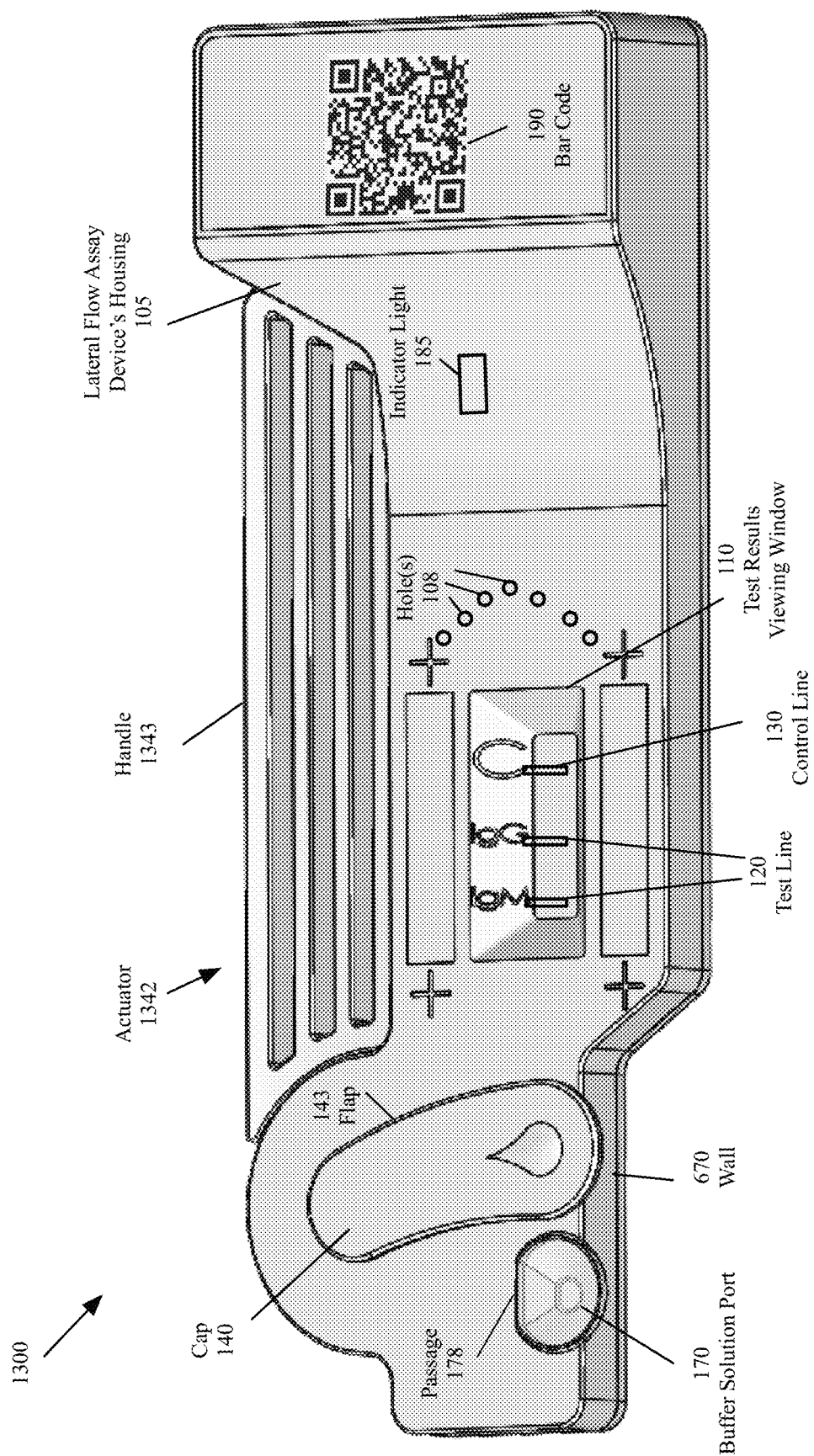

FIGS. 13A-13B illustrate top perspective views of an example lateral flow assay device with a cap and a sealer for applying a predetermined quantity of a sample through the sample port and an actuator with a rotating handle, according to various aspects of the present disclosure. With reference to FIGS. 13A-13B, the lateral flow assay device 1300 may include a housing 105, one or more holes 108, a test results viewing window 110, one or more test lines 120, a control line 130, a cap 140, a flap 143, a sample port 165, a rim 167, a buffer solution port 170, passages 168 and 178, a sealer 180, an indicator light 185, a bar code 190, an/or an NFC chip (not shown), which may be similar to the corresponding components of FIGS. 1A-1B and 9.

The lateral flow assay device 1300 may include an actuator 1342, which may include a rotating handle 1343. The lateral flow assay device 1300 may include capillary pads such as sample pad, conjugate pad, membrane, wicking pad, and/or filter pad. In FIGS. 13A-13B, the rotating handle 1343 of the actuator 1342 is at rest against the lateral flow assay device's housing 105. For example, the rotating handle 1343 may be at rest in a groove 1360 in the lateral flow assay device's housing 105.

FIG. 13A shows the lateral flow assay device 1300 with the cap 140 opened. FIG. 13B shows the lateral flow assay device 1300 with the cap 140 closed, covering the sample port 165. For example, FIG. 13B may show the lateral flow assay device after a quantity of sample is applied to the sample port and the cap 140 is closed to start the test. The cap 140 may be connected to a flap 143 that may rotate in order to open or close the sample port 165.

As shown in FIG. 13A, the edge 1311 of the flap 143 extends beyond the sealer 180. When the sealer 180 is pushed into the passage 168 and snapped in, the extension of the edge 1311 of the flap 143 keeps the extra sample volume that is pushed out of the passage 168 from splashing out over the body of the cartridge and keeps the extra sample volume confined to the area near and under the top of the flap 143.

Figure 14A:
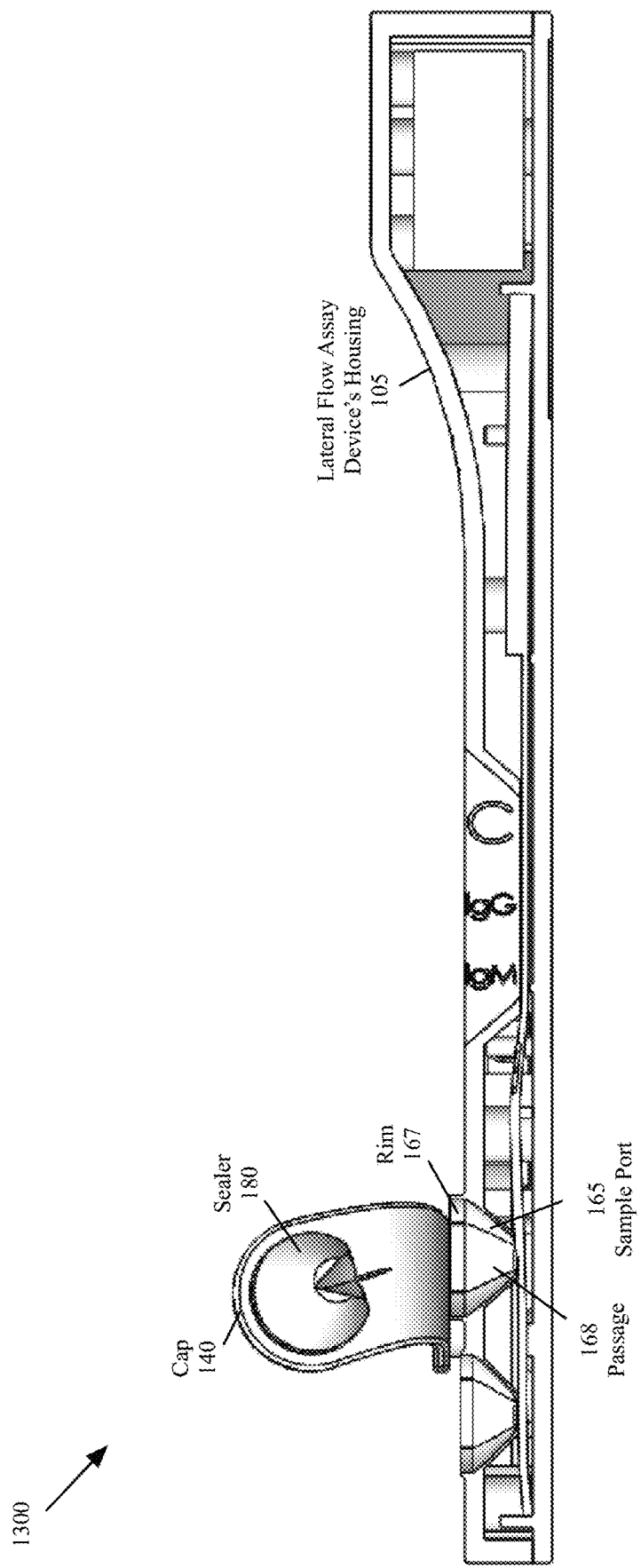
FIG. 14A illustrates a front elevation cross sectional view of the lateral assay device of FIGS. 13A-13B when the cap is open, according to various aspects of the present disclosure.
Figure 14B:
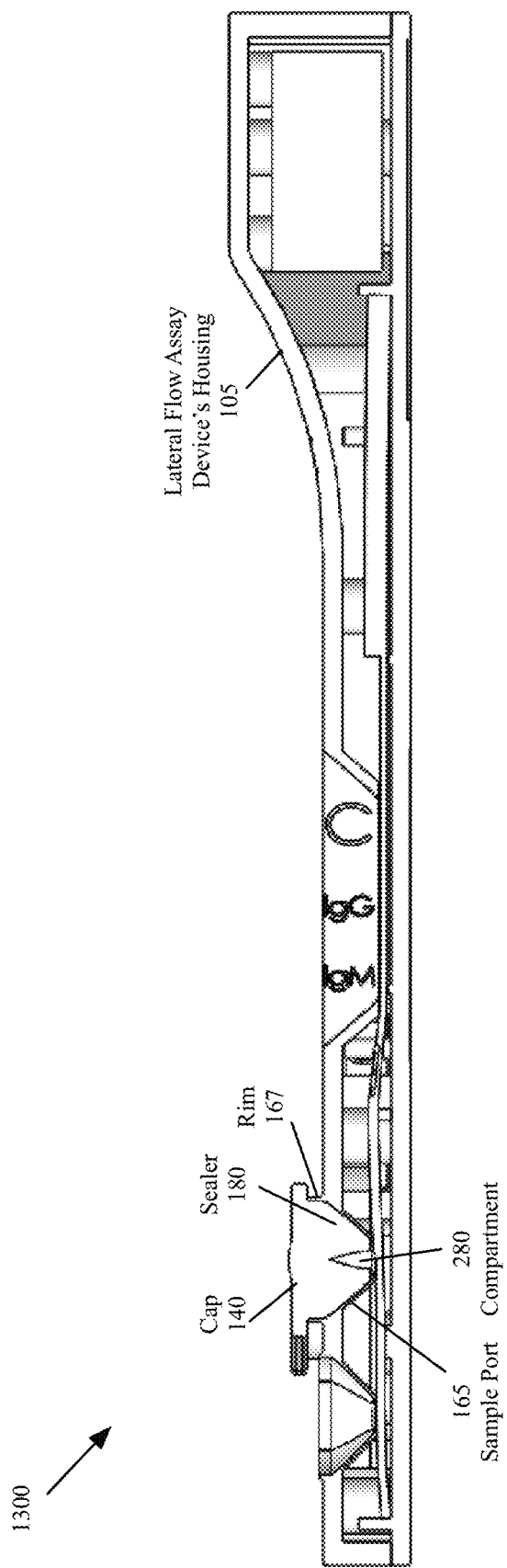
FIG. 14B illustrates a front elevation cross sectional view of the lateral assay device of FIG. 14A when the cap is closed, according to various aspects of the present disclosure.

FIG. 14A illustrates a front elevation cross sectional view of the lateral assay device of FIGS. 13A-13B when the cap is open, according to various aspects of the present disclosure. FIG. 14B illustrates a front elevation cross sectional view of the lateral assay device of FIG. 14A when the cap is closed, according to various aspects of the present disclosure.

With reference to FIGS. 14A-14B, when the cap 140 is closed, the sealer 180 may snuggly fit inside the passage of the sample port 165 such that a compartment 280 with a predetermined volume is formed between the sealer 180 and the sample port 165. Depending on the type of the test performed by the lateral flow assay device 100, the shape and the size of the sample port 165, the shape of the cap 140, and the shape and the size of the sealer 180 are configured such that the compartment 280 may have a predetermined volume that may be required for the test, and may hold an amount of sample fluid that does not exceed the predetermined volume.

Any amount of the sample fluid that does not fit inside the compartment 280 may be pushed out of the sample port by the sealer 180. For example, in some embodiments, the extra sample fluid may be pushed over the sample port's rim 167 and may be kept under the cap 140. In some embodiments, the lateral flow assay device's housing 105 may include a groove (not shown) around the sample port 165 to hold the additional sample fluid that may be pushed out of the sample port by the sealer 180. The rim 167 may create an edge around the sample port 165 that is raised over the surface of the housing 105 and may prevent the additional sample fluid that is pushed out of the sample port 165 to return into the sample port's passage 168. Once the sample fluid is applied to the sample port 165 and the cap 140 is closed, the sample port's passage 168 may hold the sample until the actuator 1342 is activated, as described below with reference to FIGS. 15A-15B.

Figure 15A:
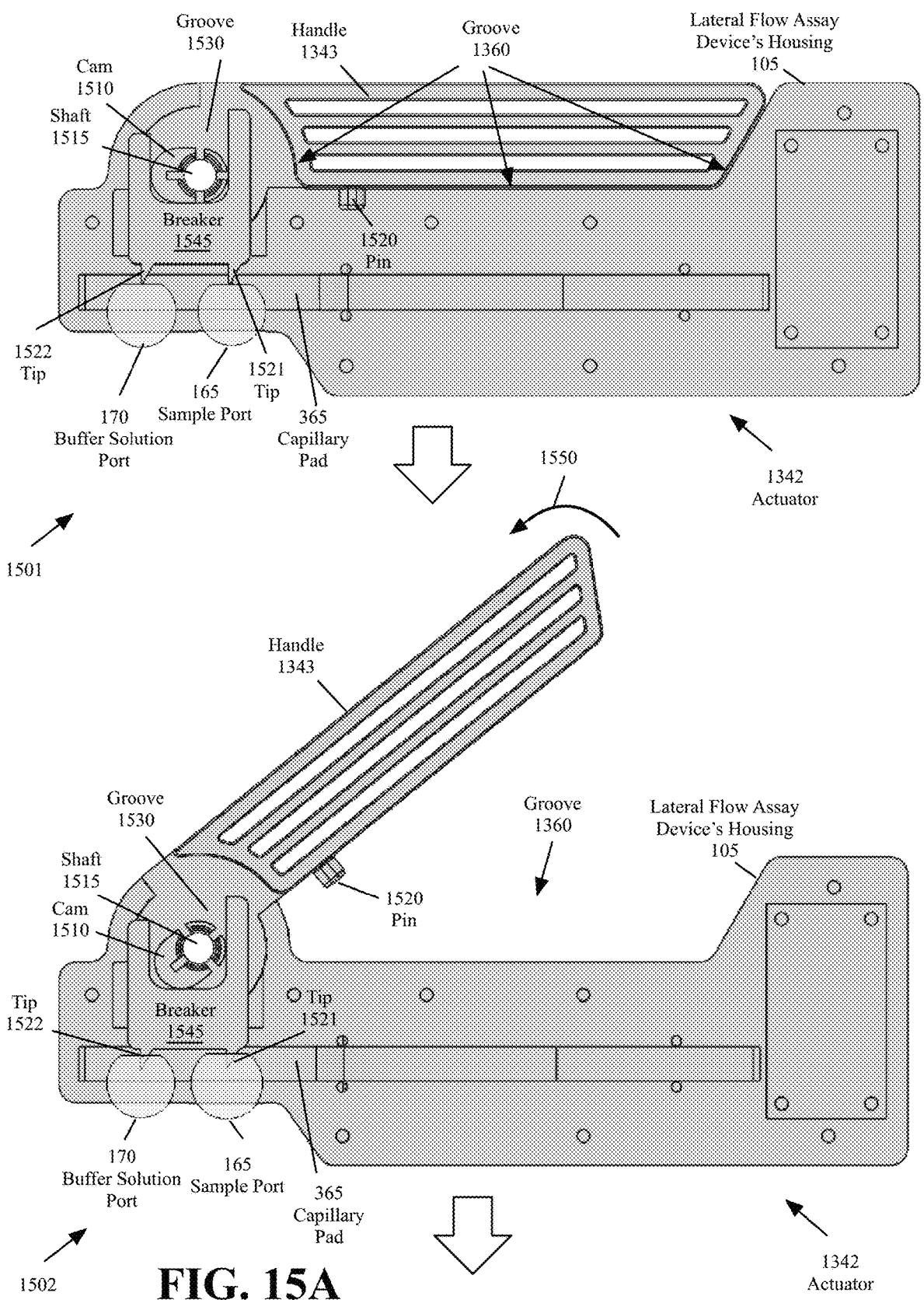
FIGS. 15A-15B illustrate a top cross sectional view of an example breaker of a lateral flow assay device that includes a rotating handle, according to various aspects of the present disclosure.
Figure 15B:
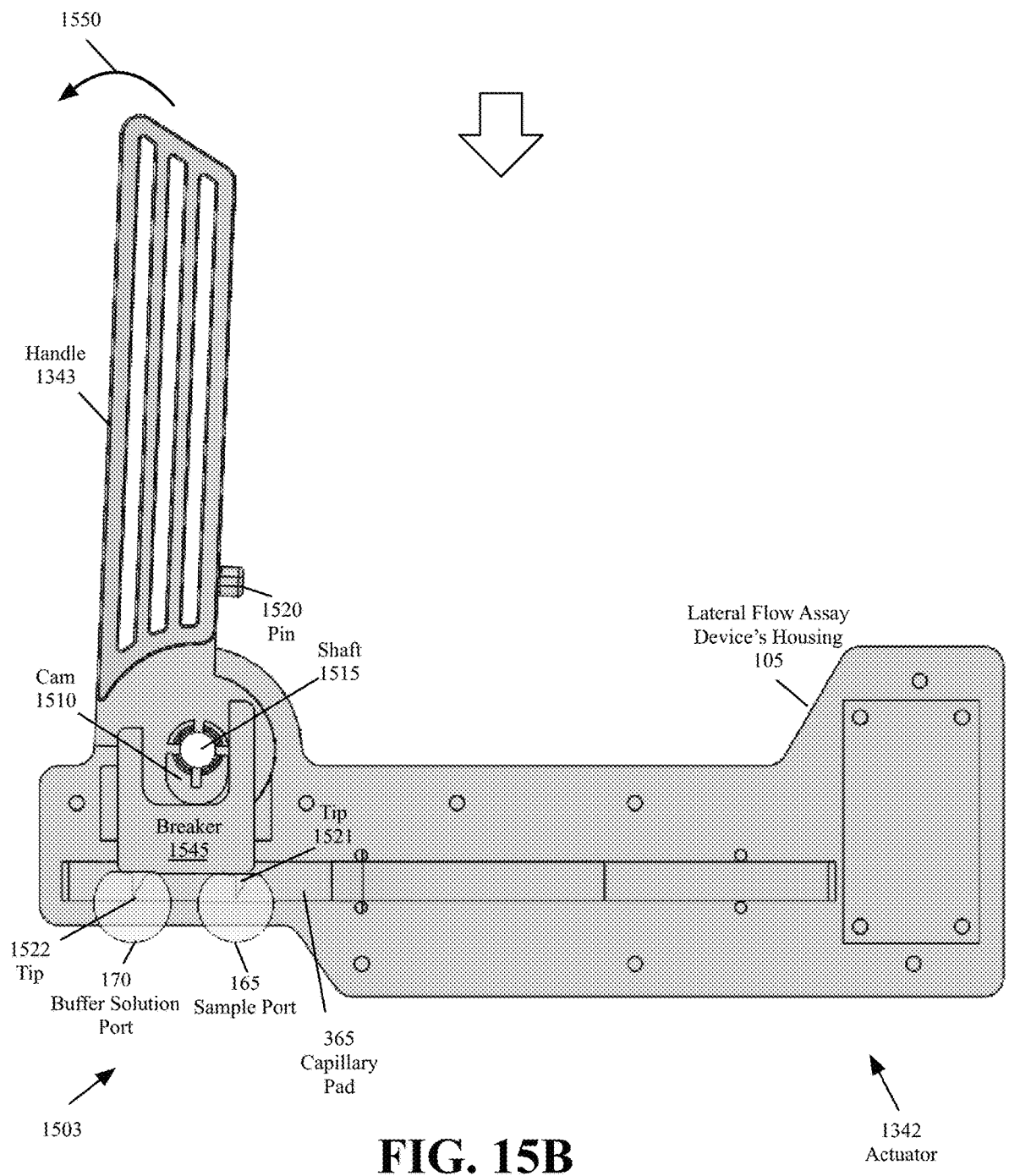
Figure 16:
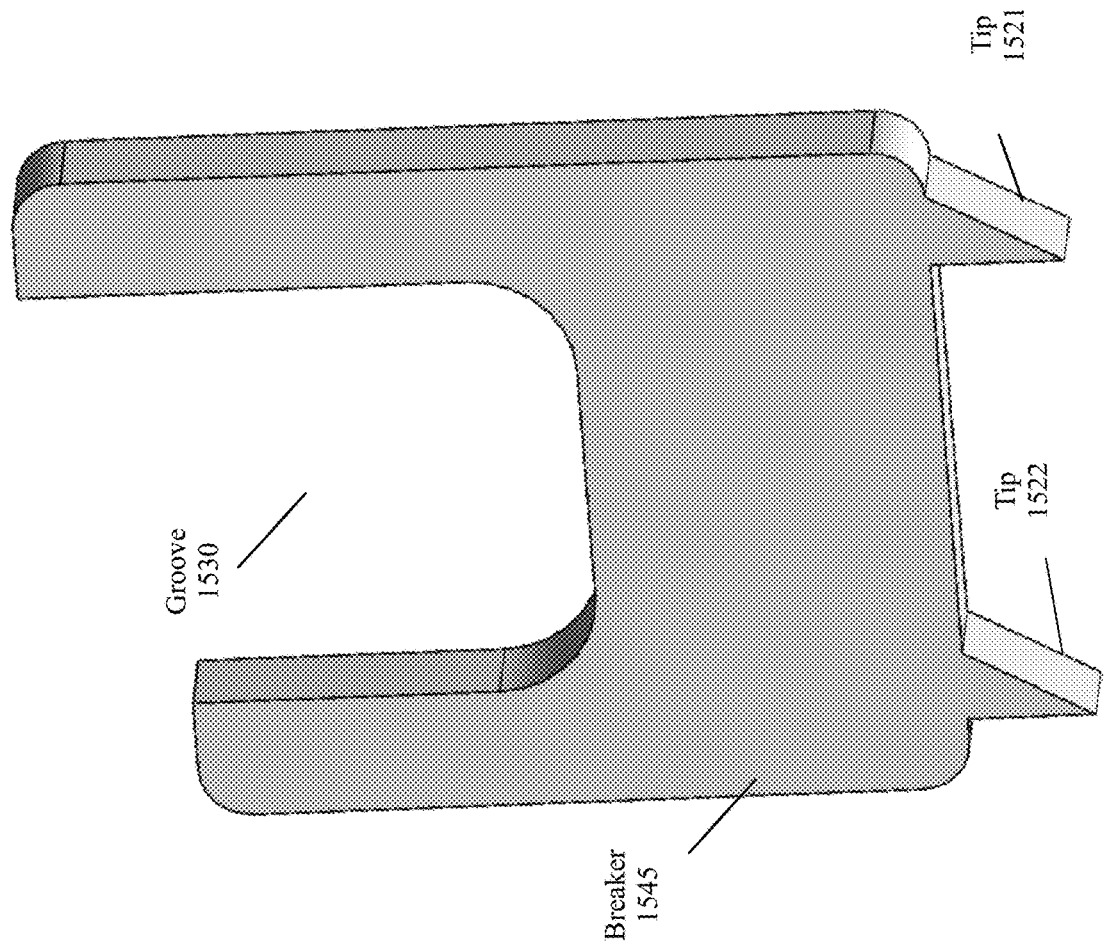
FIG. 16 illustrates a top perspective view of an example breaker of the lateral flow assay device of 15A-15B, according to various aspects of the present disclosure.

FIGS. 15A-15B illustrate a top cross sectional view of an example breaker of a lateral flow assay device that includes a rotating handle, according to various aspects of the present disclosure. With reference to FIGS. 15A-15B, the actuator 1342 may include the rotating handle 1343, a cam 1510, and a shaft 1515. The actuator 1342 may include, and/or may be attached to, a breaker 1545. FIG. 16 illustrates a top perspective view of an example breaker of the lateral flow assay device of 15A-15B, according to various aspects of the present disclosure. With reference to FIG. 16, the breaker 1545 may include the tips 1521-1522 and the groove 1530.

The cam 1510 may be configured to rotate with the rotating handle 1343 such that when the rotating handle 1343 is rotated for a certain angular value, the cam 1510 may also rotate for the same angular value. In some embodiments, the cam 1510 and the shaft 1515 may be fixedly attached to the rotating handle 1343. In other embodiments, the cam 1510 may be fixedly attached to the shaft 1515, and the shaft 1515 may be fixedly attached to the rotating handle 1343. Yet, some embodiments may not include the shaft 1515. In these embodiments, the cam 1510 may be fixedly attached to the rotating handle 1343.

FIGS. 15A-15B, as shown, include three operational stages 1501-1503. In stage 1501, the rotating handle 1343 may be at rest close to, or against, the lateral flow assay device's housing 105. For example, in the depicted embodiments, the rotating handle 1343 may be at rest in the groove 1360 in the lateral flow assay's housing 105.

The cam 1510 may be positioned inside the breaker's groove 1530 and may be configured to convert the rotary motion of the rotating handle 1343 into a linear motion of the breaker 1545. For example, the cam 1510 may be configured such that when the rotating handle 1343 is at rest close to, or against, the lateral flow assay's housing 105 (as shown in stage 1501), the breaker's tips 1521-1522 may be close to, or may be touching, the exterior of the cavity surface of the sample port 165 and the exterior of the cavity surface of the buffer solution port 170, respectively. The tips 1521 and 1522, in stage 1501, may not apply any pressure to break the cavity surfaces of the sample port 165 and the buffer solution port 170.

In stage 1501, any sample fluid that is applied into the sample port 165 may be kept in the passage 168 (FIGS. 13A-13B) without getting in contact with the capillary pad 365 of the lateral flow assay device 1300. In the embodiments that include a sample pad, the capillary pad 365 may be the sample pad. In the embodiments that do not include a sample pad, the capillary pad 365 may be the conjugate pad. In the embodiments that include a plasma separator filter (red blood cell filter) the capillary pad 365 may be the filter pad.

In stage 1502, the rotating handle 1343 may be rotated away from the lateral flow assay's housing 105 in the direction of the arrow 1550. The cam 1510 and the shaft 1515, which are fixedly attached to the rotating handle 1343, may rotate with the rotating handle 1343. The cam 1515 is configured such that, when the cam 1515 rotates in the direction of the arrow 1550 (e.g., when the handle 1343 is rotating away from the housing 105), the cam 1510 may push (e.g., to linearly move) the breaker 1545 towards the sample port 165 and the solution port 170. The tips 1521 and 1522 may apply pressure to the exterior of the cavity surfaces of the sample port 165 and the buffer solution port 170, respectively. As shown in stage 1502, the tips 1521 and 1522 may have made a hole in the cavity surfaces of the sample port 165 and the buffer solution port 170, respectively.

In some embodiments, at least a portion of the cavity surface of the sample port (e.g., a portion of a wall of the cavity surface) and/or at least a portion of the cavity surface of the buffer solution port (e.g., a portion of a wall of the cavity surface) may be made from a material that may break when the tips 1521 and 1522 apply pressure to the corresponding walls. In other embodiments, the cavity surface (e.g., a wall of the cavity surface) of the sample port and/or the cavity surface (e.g., a wall of the cavity surface) of the buffer solution port's wall may include breakable tabs that may break when the tips 1521 and 1522 apply pressure to the corresponding tabs.

The rotating handle 1343, in stage 1503, may have rotated in the direction of the arrow 1550 further away for its rest position. The cam 1510 may be configured to further push the breaker 1545 towards the sample port 165 and the solution port 170. The tip 1521, in stage 1503, may have made a hole in the cavity surface of the sample port 165 that may be enough to allow the sample liquid in the sample port 165 to be applied to the capillary pad 365. The tip 1522, in stage 1503, may have made a hole in the cavity surface of the buffer solution port 170 that may be enough to allow the buffer solution liquid in the buffer solution port 170 to be applied to the capillary pad 365.

Although the lateral assay device 1500 described above included a buffer solution port 170, some embodiments may not include a buffer solution port. In these embodiments, the breaker 1545 may only include the tip 1521. Depending on the type of test and the type of the sample, a buffer solution may not be needed or the buffer solution may be applied through the sample port prior to closing the cap 140 (FIGS. 13A-13B).

Similar to the lateral flow assay device 100 of FIGS. 6 and 7, the lateral flow assay device 1300 may include some or all of the electronic circuitry 600, such as, a timer 605, an audible alarm indicator 615, a visual alarm indicator 620, a processor 625, one or more batteries 630, a switch 650, one or more wireless transceivers 680, and/or a GPS receiver 685. The electronic circuitry may include additional components, such as, for example, and without limitations, capacitors, resistors, solenoids, buffers, etc. The lateral flow assay device 1300 may also include a spring 660, similar to the spring 660 of FIG. 6. The sample port 165 of the lateral flow assay device 1300 may be close to an edge of the lateral flow assay device 1300, for example close to the wall 670 to facilitate applying blood sample to the sample port 165.

The lateral flow assay device 1300, in some of the embodiments that include some or all of the circuitry 600, may include a pin 1520 (FIGS. 15A-15B). The pin 1520 may be configured to connect the battery (or batteries) 630 to the rest of the electronic circuitry 600 components prior to start of a test. For example, the pin 1520 may sit against a normally open switch (e.g., similar to the switch 650 of FIGS. 6 and 7) that keeps the battery (or batteries) 630 disconnected from the rest of the electronic circuitry 600 prior to start of a test (e.g., to save the battery life). The switch may include a spring (e.g., similar to the spring 660 of FIGS. 6 and 7). Once the handle 1343 is rotated, the pin 1520 is moved away from the spring of the switch and connects the battery (or batteries) 630 to the other components of the electronic circuitry 600.

Figure 17A:
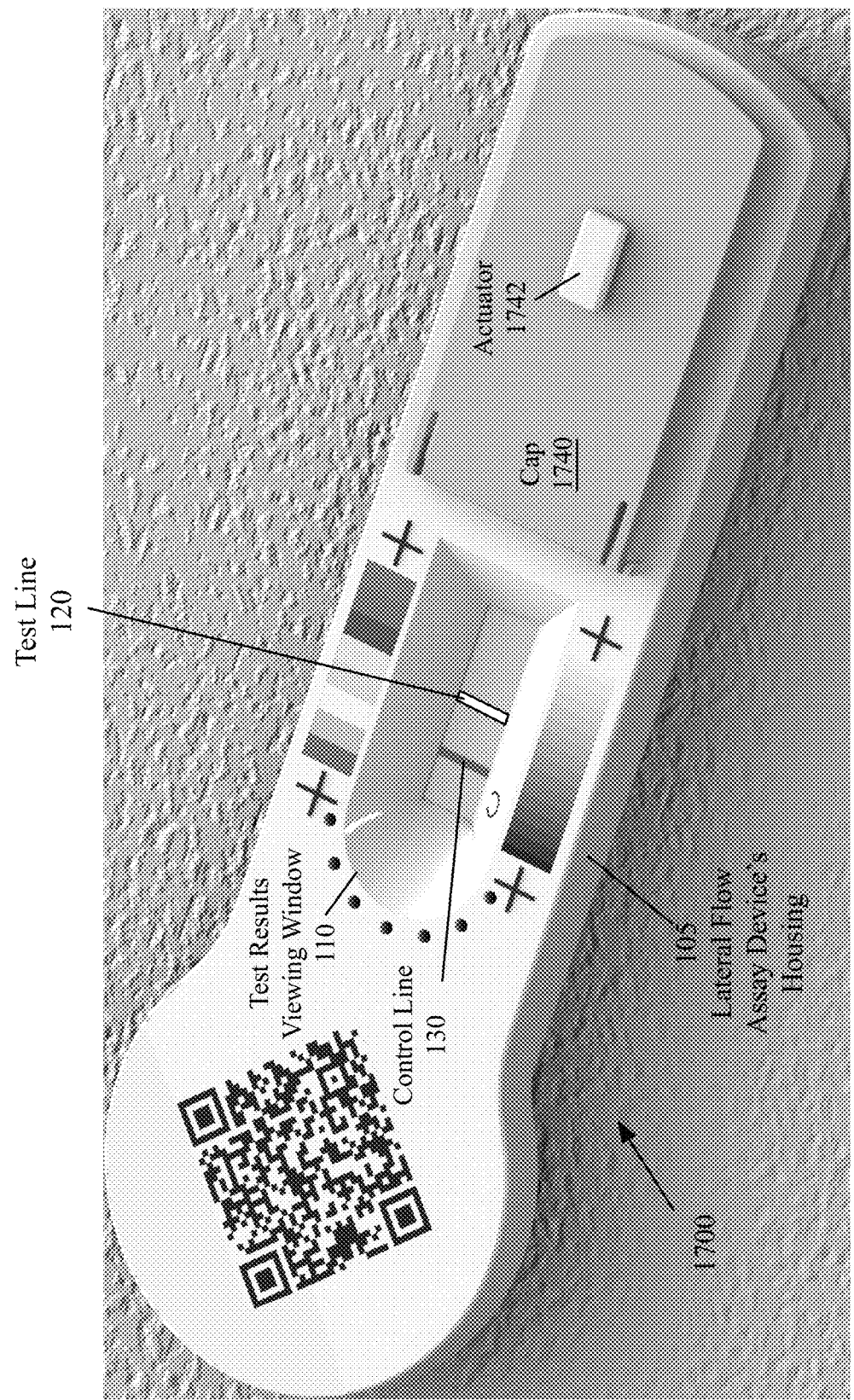
FIGS. 17A-17C show top perspective views of an example lateral flow assay device with a cap and a sealer for applying a predetermined quantity of a sample through the sample port, according to various aspects of the present disclosure.
Figure 17B:
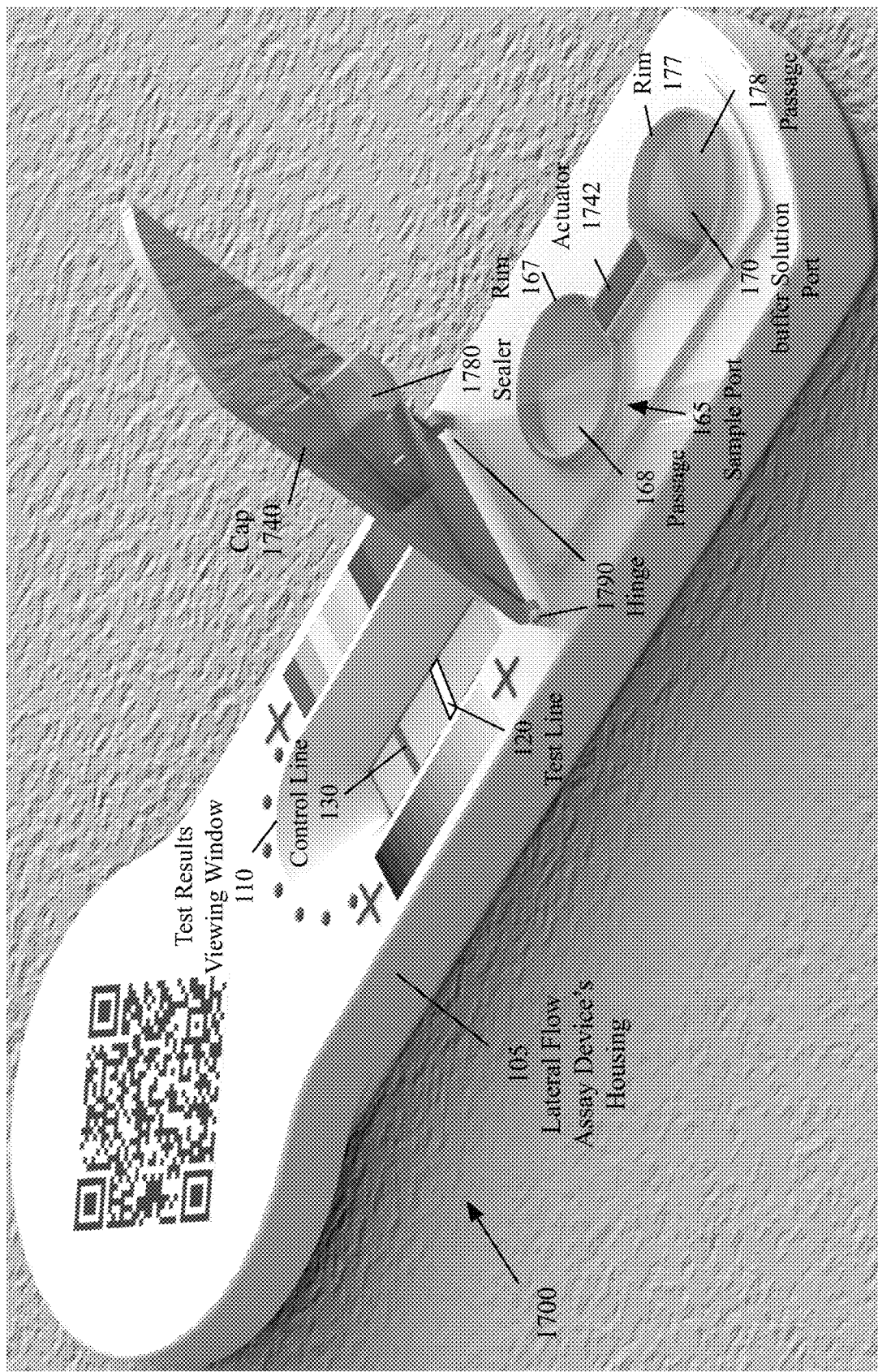
Figure 17C:
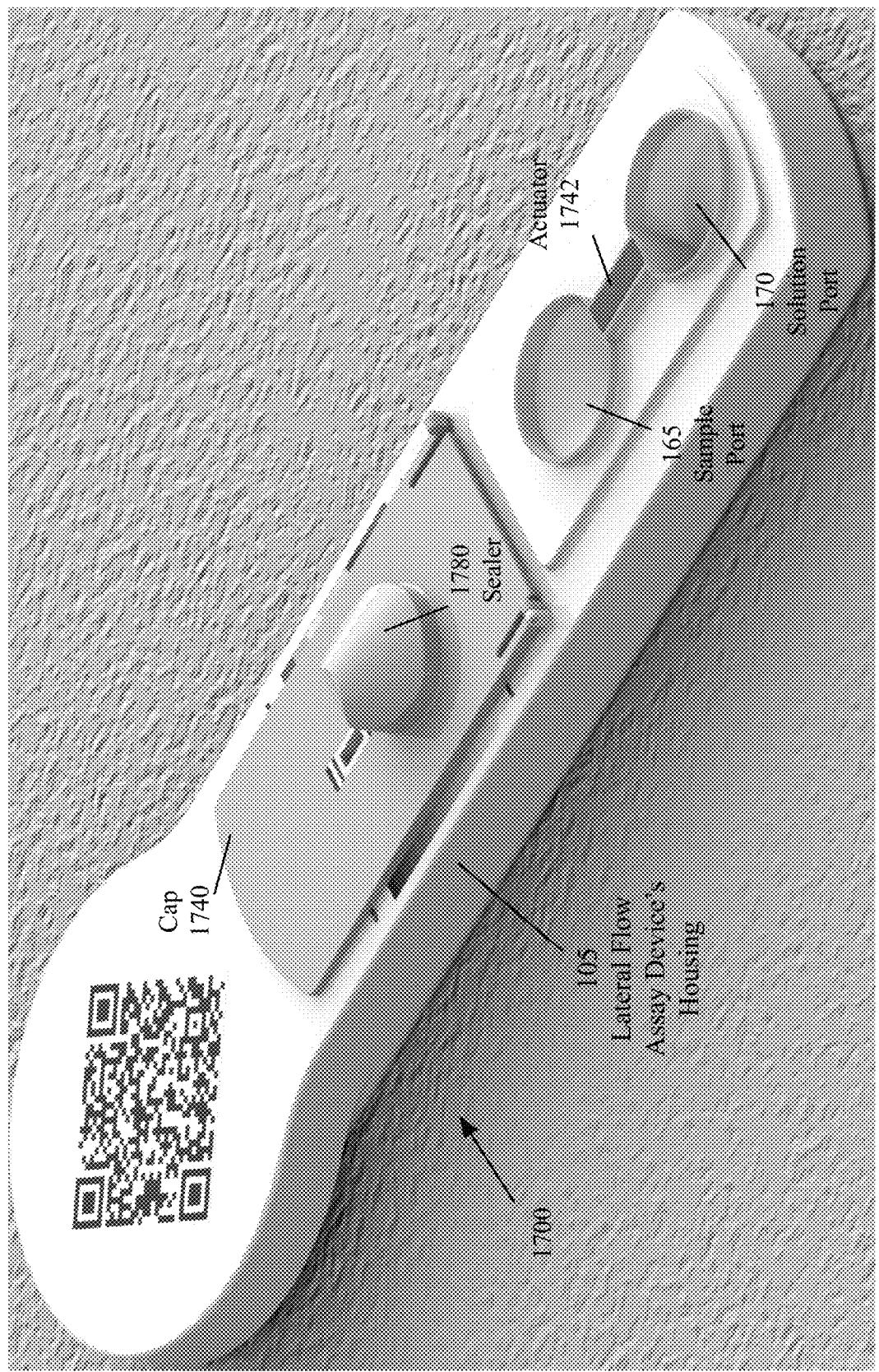

In some embodiments, the actuator may include a push-in button and the portion of the breaker that includes the tips may be made of elastic material. FIGS. 17A-17C show top perspective views of an example lateral flow assay device with a cap and a sealer for applying a predetermined quantity of a sample fluid through the sample port, according to various aspects of the present disclosure. With reference to FIG. 17A-17C, the lateral flow assay device 1700 may include a housing 105, a test results viewing window 110, one or more test lines 120, a control line 130, a cap 1740, an actuator 1742, a sample port 165, a buffer solution port 170, and a sealer 1780.

FIG. 17A shows the lateral flow assay device 1700 with the cap 1740 closed, covering the sample and the buffer solution ports. For example, FIG. 17A may show the lateral flow assay device after a quantity of sample is applied to the sample port and the cap 1740 is closed to start the test.

FIG. 17B shows the cap 1740 is being opened or closed. As shown, the cap 1740 may rotate around the hinges 1790. FIG. 17C shows the cap 1740 being fully opened, for example, to apply sample fluid to the sample port 165. FIG. 17C may also show the lateral flow assay device prior to the start of a test and after applying the sample to the sample port. The sample port 165 may include a rim 167 and a passage 168.

When the sample fluid required for the test is blood, a person may punch a fingertip with a lancet and may simply and easily press the fingertip against the rim 167 of the sample port 165 to apply a quantity of blood to the sample port's passage 178. This eliminates the need for using a pipette or other sampling devices to pick the blood from the finger and place it in the sample port. Disposable pipettes intended for use in home test kits are often difficult to use and lead to errors in obtaining the correct amount of sample which can result in errors in the outcome of the test. The passage 168 may be a tube (which may be, e.g., and without limitations, at least partially funnel shaped). The buffer solution port 170 may include a passage 178. The passage 178 may be a tube (which may be, e.g., and without limitations, at least partially funnel shaped).

As described below, the passage 168 may be configured such that the passage 168 may hold the sample fluid until a hole is punched in the cavity surface of the passage 168 in order for the sample fluid to be applied to the lateral flow assay device's capillary pads. The passage 178 may be configured such that the passage 178 may hold the buffer solution until a hole is punched in the cavity surface of the passage 178 in order for the buffer solution to be applied to the lateral flow assay device's capillary pads.

The sealer 1780 on the cap 1740 may be configured to snugly fit inside the passage of the sample port 165 such that a predetermined amount of sample fluid may be trapped inside the sample port's passage 168 and any additional amount of sample fluid may be blocked by the sealer 180 from reaching the lateral flow device's capillary pads.

Figure 18:
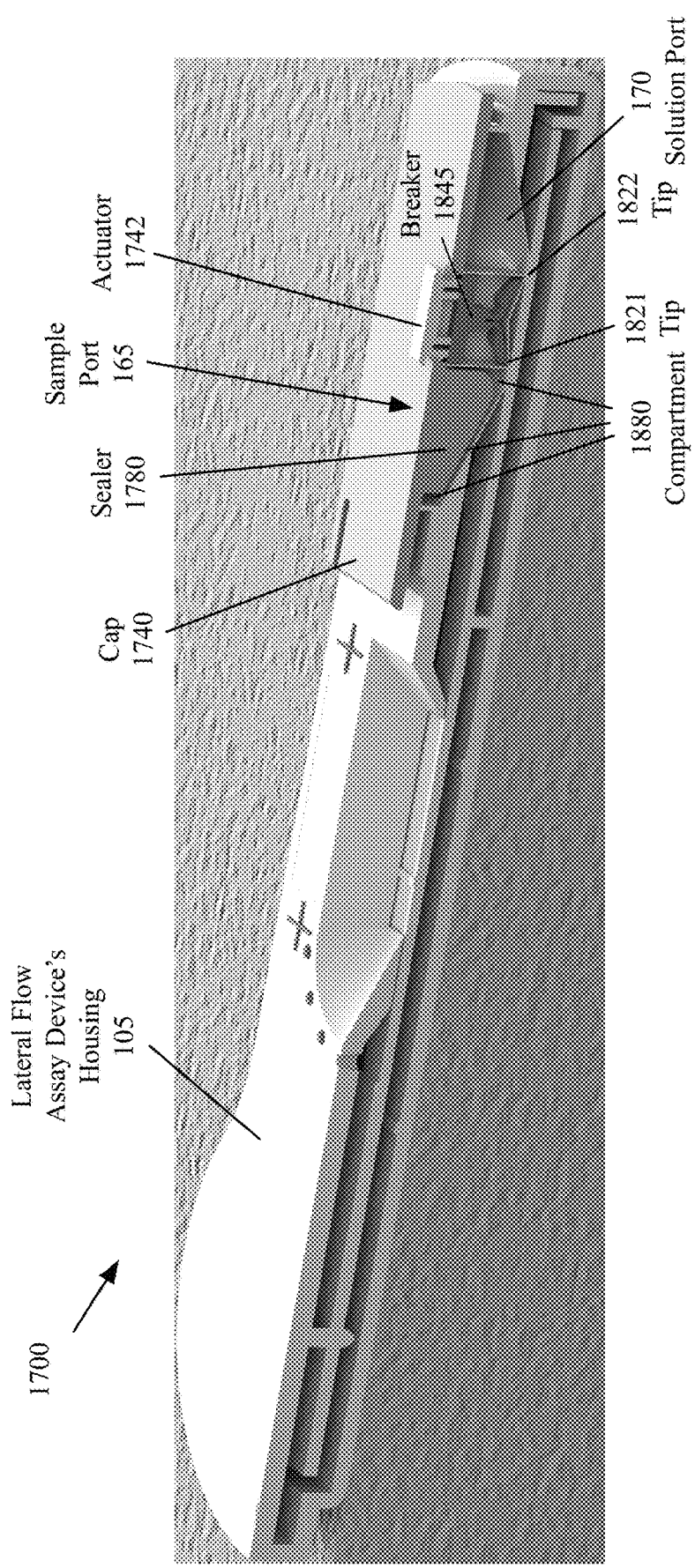
FIG. 18 illustrates a front perspective cross sectional view of the lateral assay device of FIGS. 17A-17C showing the cap being closed, according to various aspects of the present disclosure.
Figure 19:
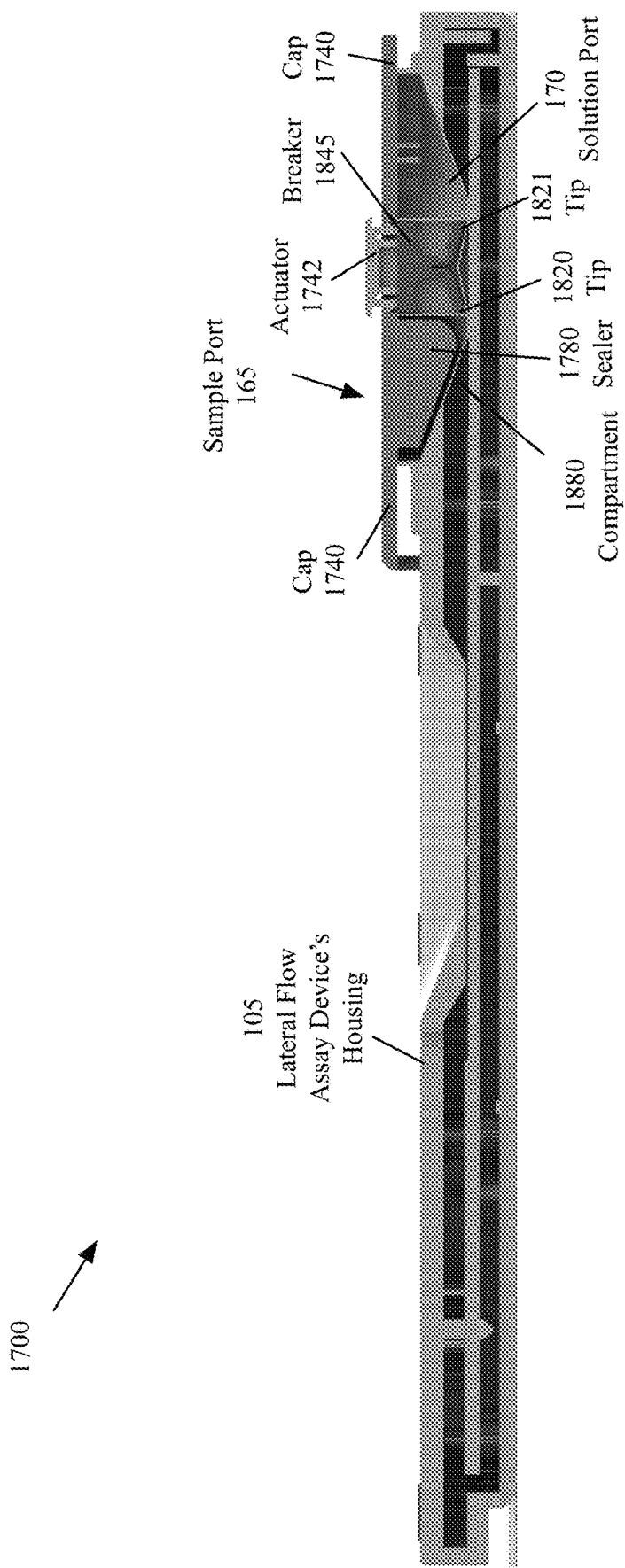
FIG. 19 illustrates a front elevation view of the lateral assay device of FIG. 18, according to various aspects of the present disclosure.

FIG. 18 illustrates a front perspective cross sectional view of the lateral assay device of FIGS. 17A-17C when the cap is closed, according to various aspects of the present disclosure. FIG. 19 illustrates a front elevation view of the lateral assay device of FIG. 18, according to various aspects of the present disclosure.

With reference to FIGS. 18-19, when the cap 1740 is closed, the sealer 1780 may snuggly fit inside the passage of the sample port 165 such that a compartment 1880 with a predetermined volume is formed between the sealer 1780 and the sample port 165. Depending on the type of the test performed by the lateral flow assay device 1700, the shape and the size of the sample port 165, the shape of the cap 1740, and the shape and the size of the sealer 1780 are configured such that the compartment 1880 has a predetermined volume that may be required for the test, and may hold an amount of sample fluid that does not exceed the predetermined volume.

Figure 20:
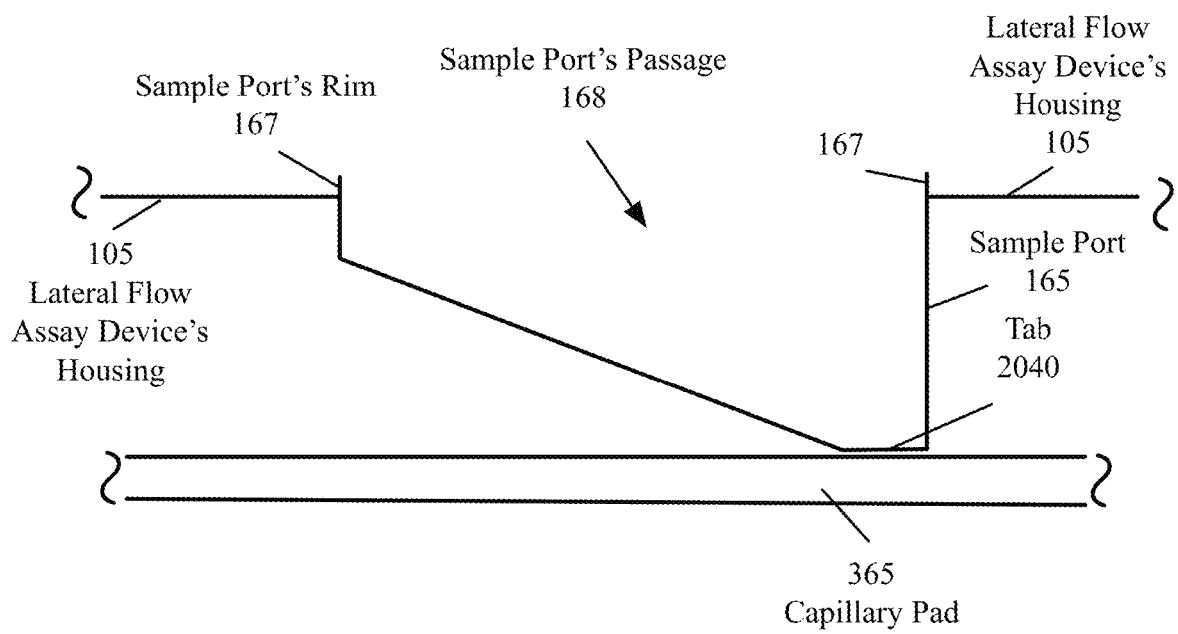
FIG. 20 is a front elevation view of the cross section of an example sample port of a lateral flow assay device, according to various aspects of the present disclosure.

FIG. 20 is a front elevation view of the cross section of an example sample port of a lateral flow assay device, according to various aspects of the present disclosure. With reference to FIG. 20, the sample port 165 may include a passage 168, a tab 2040, and a rim 167. The tab 2040 may be breakable. Prior to the tab 2040 being broken, any sample fluid that may be applied into the sample port 165 may be kept in the passage 168 without getting in contact with the capillary pad 365 of the lateral flow assay device. In the embodiments that include a sample pad, the capillary pad 365 may be the sample pad. In the embodiments that do not include a sample pad, the capillary pad 365 may be the conjugate pad. In the embodiments that include a plasma separator filter (red blood cell filter) the capillary pad may be the filter pad.

Figure 21:
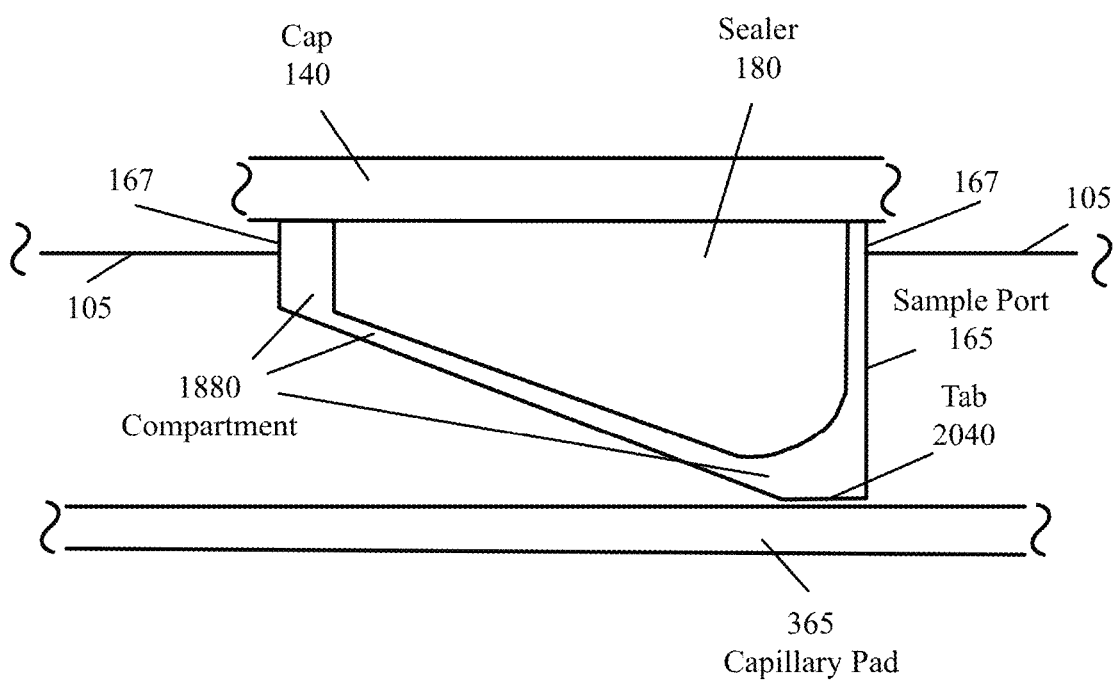
FIG. 21 is a front elevation view of the cross section of the sample port of FIG. 20 after the cap is closed, according to various aspects of the present disclosure.

FIG. 21 is a front elevation view of the cross section of the sample port of FIG. 20 after the cap is closed, according to various aspects of the present disclosure. With reference to FIG. 21, after the cap 1740 is closed, the sealer 1780 may fit inside the passage 168 (FIG. 20) of the sample port 165. The sealer 1780, the sample port 165, and the cap 1740 may form a compartment 1880. As described above, the sealer 1780, the sample port 165, and the cap 1740 may be configured such that the compartment 1880 may hold a predetermined volume of sample fluid as required by the test performed by the lateral flow assay device.

Any amount of sample fluid that does not fit inside the compartment 1880 may be pushed out of the sample port by the sealer 1780. For example, the extra sample fluid may be pushed over the sample port's rim 167 and may be kept under the cap 1740. In some embodiments, the lateral flow assay device's housing 105 may include a groove (not shown) around the sample port 165 to hold the additional sample fluid that may be pushed out of the sample port by the sealer 1780. The rim 167 may create an edge around the sample port 165 that is raised over the surface of the housing 105 and may prevent the additional sample fluid that is pushed out of the sample port 165 to return into the sample port's passage 168. Once the sample fluid is applied to the sample port 165 and the cap 1740 is closed, the sample port's passage 168 may hold the sample until the tab 2040 is broken.

Figure 22:
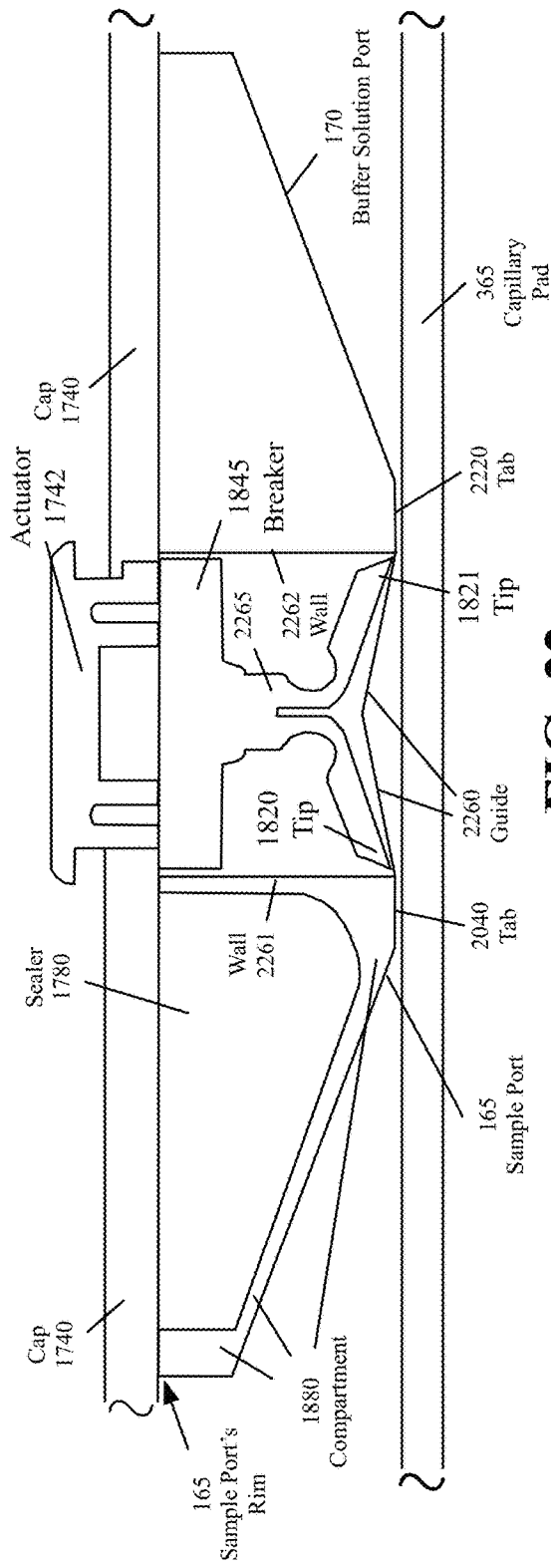
FIG. 22 is a front elevation view of the cross section of the sample port, the buffer solution port, the actuator, and the breaker of FIGS. 18 and 19, according to various aspects of the present disclosure.

With reference to FIGS. 18 and 19, the actuator 1742 may be a button (e.g., a push button) that may be connected to the breaker 1845. The breaker 1845 may include two tips 1821 and 1822. FIG. 22 is a front elevation view of the cross section of the sample port, the buffer solution port, the actuator, and the breaker of FIGS. 18 and 19, according to various aspects of the present disclosure.

With reference to FIG. 22, the buffer solution port 170 may include a tab 2220. As long as the tab 2220 is not broken, the buffer solution port 170 may hold the buffer solution inside the buffer solution port 170 without allowing the buffer solution to reach the capillary pad 365.

With further reference to FIG. 22, the breaker 1845 may include the tips 1820 and 1821. The tips may rest on the guide's 2260 surface. The breaker 1845 may be configured such that the portion of the breaker 1845 that includes the tips 1820 and 1821 is elastic. As the actuator 1742 is pressed and the breaker 1845 is pushed down (e.g., is pushed towards the capillary pad 365) against the guide 2260, the tips 1820 and 1821 may move away from the shaft 2265 of the breaker 1845 and towards the cavity surface 2261 of the sample port 165 and the cavity surface 2262 of the buffer solution port 170, respectively.

Figure 23:
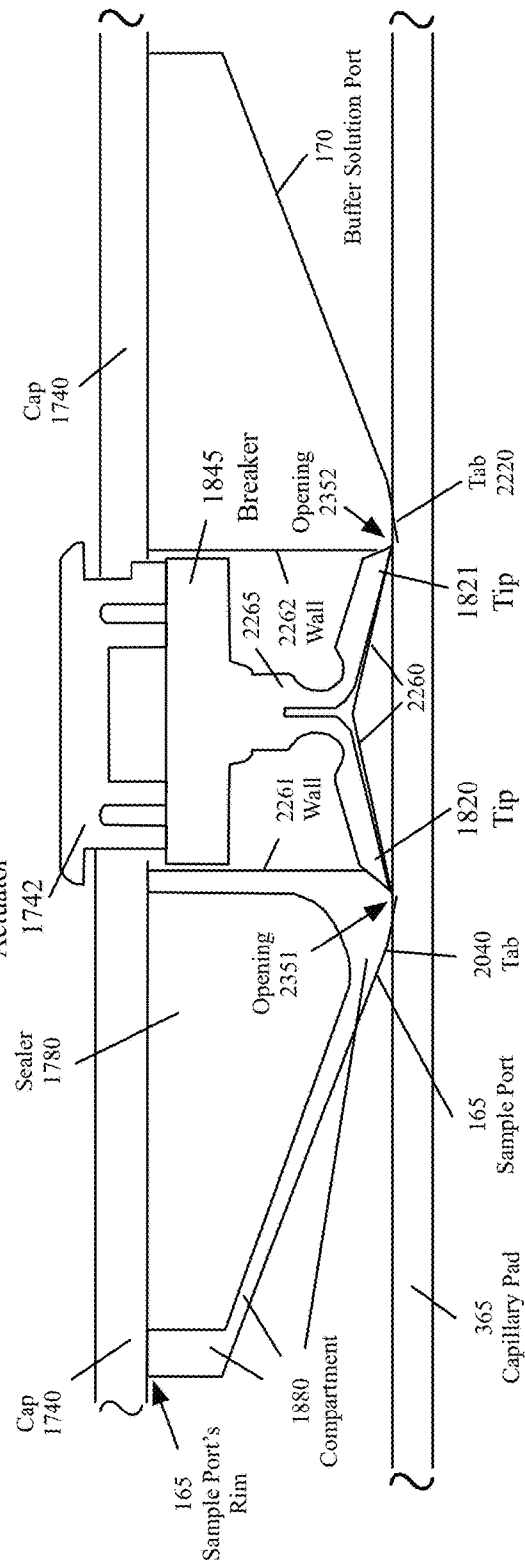
FIG. 23 is a front elevation view of the cross section of the sample port, the buffer solution port, the actuator, and the breaker of FIG. 22 after the actuator is pushed down, according to various aspects of the present disclosure.

FIG. 23 is a front elevation view of the cross section of the sample port, the buffer solution port, the actuator, and the breaker of FIG. 22 after the actuator is pushed down, according to various aspects of the present disclosure. As shown, when the breaker 1845 is pushed down by the actuator 1745, the tips 1820 and 1821 are pushed away from the shaft 2265 and towards the cavity surfaces, for example, the walls 2261 and 2262, respectively. The tabs 2040 and 2220 may be configured to be breakable. The tips 1820 and 1821 may apply force to, and break, the tabs 2040 and 2220, respectively.

Once the tab 2040 is broken, the opening 2351 may allow the sample fluid in the compartment 1880 to be applied, for example, by gravity as well as the capillary action of the pad material, to the capillary pad 365. Once the tab 2220 is broken, the opening 2352 may allow the buffer solution in the buffer solution port 170 to be applied, for example, by gravity as well as the capillary action of the pad material, to the capillary pad 365.

Although the embodiments of FIGS. 22 and 23 show a breakable tab 2040 in the sample port and a breakable tab 2220 in the buffer solution port that may be broken in order to apply the sample fluid and the buffer solution to the capillary pad 365, in other embodiments one or both of the tabs 2040 and 2220 may be replaced by thin, breakable walls. In these embodiments, at least a portion of the cavity surfaces (e.g., the walls 2261 and 2262) may be configured to be thin and breakable. Pressing the tips 1820 and 1821 against the walls 2261 and 2262 may break the walls 2261 and 2262, respectively.

Figure 24:
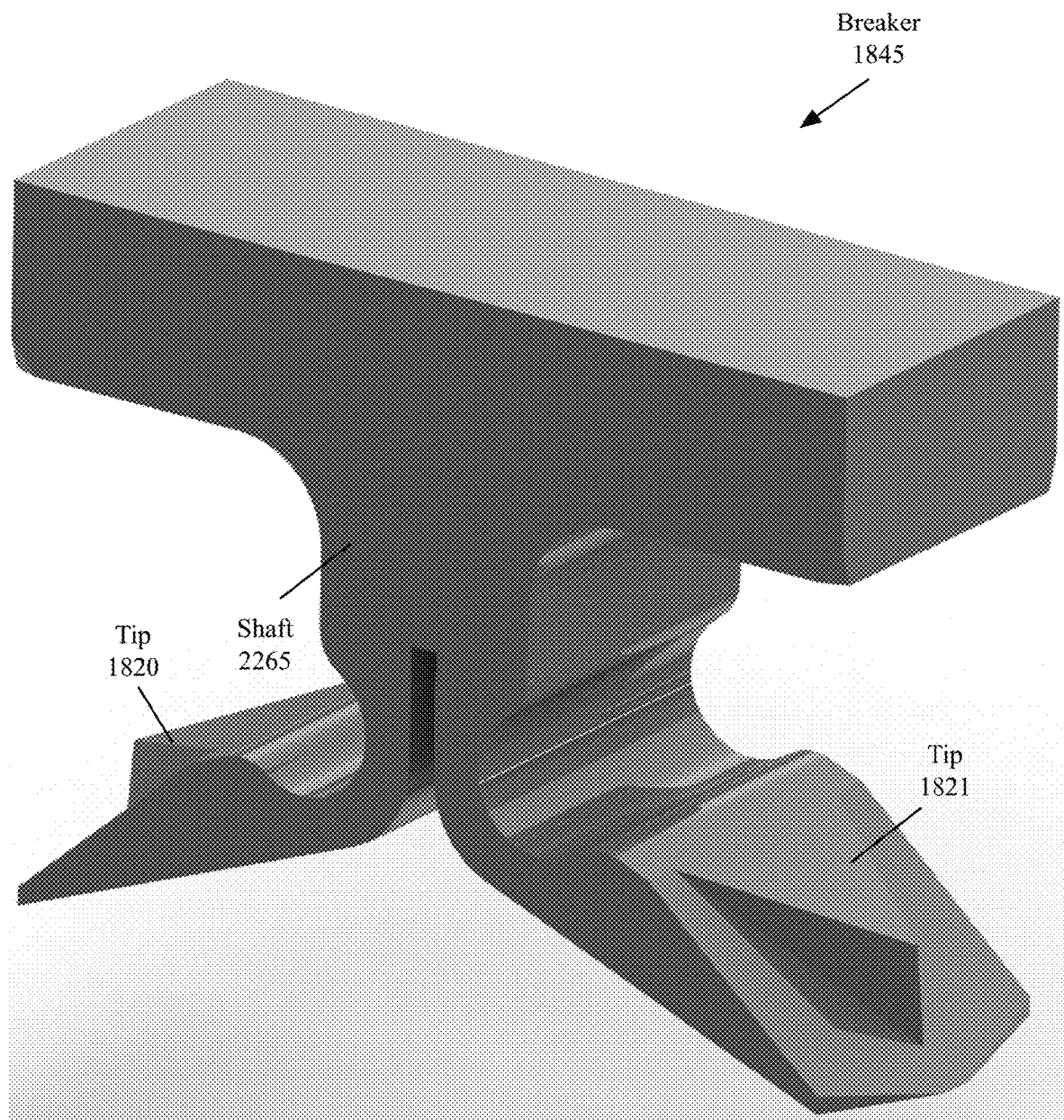
FIG. 24 is a front perspective view of the breaker of a lateral flow assay device, according to various aspects of the present disclosure.

FIG. 24 is a front perspective view of the breaker of a lateral flow assay device, according to various aspects of the present disclosure. As shown, the breaker 1845 may include the tips 1820 and 1821. At least the portion of the breaker 1845 that includes the tips 1820 and 1821 may be elastic such that pushing the tips 1820 and 1821 against a surface (e.g., the guide 2260 of FIGS. 22 and 23) may cause the tips 2220 and 2221 to move away from the shaft 2265.

Although the lateral assay device 1700 described above included a buffer solution port 170, some embodiments may not include a buffer solution port. In these embodiments, the breaker 1845 may only include the tip 1820. Depending on the type of test and the type of sample, a buffer solution may not be needed or the buffer solution may be applied through the sample port prior to closing the cap 1740.

As described above, the lateral flow assay devices 100, 900, 1300, and 1700 of the present embodiments provides ease of use, especially for home test applications where the user may not have precision tools to apply a predetermined amount of sample to the sample port. The lateral flow assay device of the present embodiments, therefore, reduces the human errors by ensuring that the required amount of the sample fluid and the buffer solution are both applied to the capillary pads of the lateral flow assay device.

The lateral flow assay device of the present embodiments is configured to deliver the same volume of sample (e.g., blood) and buffer solution (as required by a given test) every time that the same model (e.g., the same configuration) of the lateral assay device is used, which makes the results repeatable and more reliable.

The lateral flow assay device of the present embodiments eliminates the need for external components, such as pipettes and buffer solution containers/droppers in a lateral flow assay test kit package. The lateral flow assay device of the present embodiments may include a lancet integrated on the side of the lateral flow assay device's housing and an alcohol pad integrated on the back of the cartridge with a protective cover that may get peeled back by the user.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. A lateral flow assay device, comprising:
   a capillary pad;
   a sample port comprising a cavity with a surface;
   the sample port configured to:
      receive a quantity of a sample fluid;
      hold the sample fluid prior to a hole made in the cavity surface; and
      apply the sample fluid to the capillary pad after the hole is made in the cavity surface;
   a breaker comprising a tip, the breaker configured to:
      receive a force to press the tip against the cavity surface of the sample port; and
      in response to receiving the force, make a hole in the cavity surface of the sample port with the tip causing the sample fluid held by the sample port to be applied to the capillary pad.

2. The lateral flow assay device of claim 1, wherein at least a portion of the cavity surface of the sample port is made of a thin and breakable material, wherein the hole is made in the thin and breakable portion of the cavity surface.

3. The lateral flow assay device of claim 1, wherein the cavity surface of the sample port comprises a breakable tab, wherein the hole is made in the cavity surface by breaking the tab.

4. The lateral flow assay device of claim 1, wherein the breaker comprises a groove, the lateral flow assay device further comprising:
   an actuator configured to apply the force to press the tip of the breaker against the cavity surface of the sample port, the actuator comprising:
   a rotating handle; and
   a cam positioned inside the breaker's groove;
   wherein the cam is configured to:
      make a same angular rotation as the rotating handle, and
      convert the angular rotation of the cam into a linear motion of the breaker,
   wherein the rotating handle is configured to rotate from a first position to a second position, causing the cam to push the breaker's tip to punch the hole in the cavity surface of the sample port.

5. The lateral flow assay device of claim 4 further comprising:
   a housing comprising a groove;
   wherein the rotating handle is configured to rest in the groove of the housing when the handle is in the first position.

6. The lateral flow assay device of claim 1 further comprising:
   an actuator configured to apply the force to press the tip of the breaker against the cavity surface of the sample port, the actuator comprising:
   a slider configured to move along a substantially straight line from a first position to a second position; and
   a ramp configured to push the breaker's tip against the cavity surface of the sample port to punch the hole in the cavity surface of the sample port as the slider is moved from the first position to the second position.

7. The lateral flow assay device of claim 1, further comprising:
   an actuator configured to apply the force to press the tip of the breaker against the cavity surface of the sample port, the actuator comprising:
   a push-in handle attached to the breaker,
   wherein the push-in handle is configured to:
      receive a force; and
      in response to receiving the force, move the breaker, causing the breaker's tip to punch the hole in the cavity surface of the sample port.

8. The lateral flow assay device of claim 1, further comprising:
an actuator configured to apply the force to press the tip of the breaker against the cavity surface of the sample port,
wherein the breaker comprises an elastic guide connected to the tip of the breaker,
wherein the actuator is configured to:
receive a force; and
apply the force to the breaker,
wherein the breaker's elastic guide is configured to:
receive the force from the actuator; and
in response to receiving the force, push the tip of the breaker to punch the hole on the cavity surface of the sample port.

9. The lateral flow assay device of claim 1, wherein the sample fluid is blood, the lateral flow assay device further comprising:
a housing,
wherein the sample port comprises a rim raising above a surface of the housing,
wherein the rim is configured to apply a quantity of blood to the sample port when a person presses a punctured fingertip against the rim.

10. The lateral flow assay device of claim 9, wherein the sample port is configured such that a portion of the rim is close to a side wall of the housing to facilitate pressing the fingertip against the rim.

11. The lateral flow assay device of claim 1 further comprising:
electronic circuitry configured to:
set a timer to a duration of a test;
start the timer at a beginning of the test; and
generate an alert when the timer expires.

12. The lateral flow assay device of claim 11, wherein the electronic circuitry comprises electronic circuitry to generate at least one of an audible alert and a visual alert.

13. The lateral flow assay device of claim 12 further comprising a housing encompassing the electronic circuitry, wherein the housing comprises a plurality of holes to facilitate a passage of the audible alert to an outside of the housing.

14. The lateral flow assay device of claim 1 further comprising:
a spring; and
electronic circuitry comprising:
a set of one or more batteries configured to provide power to a rest of the electronic circuitry of the lateral flow assay device; and
an electronic switch configured to:
connect the set of batteries to the rest of the electronic circuitry of the lateral flow assay device when the switch is closed; and
disconnect the set of batteries from the rest of the electronic circuitry of the lateral flow assay device when the switch is open;
wherein the spring is configured to:
move with the breaker;
keep the electronic switch open prior to a beginning of a test; and
close the electronic switch when the tip of the breaker punches the hole in the cavity surface of the sample port.

15. The lateral flow assay device of claim 14, wherein the electronic circuitry comprises:
a processor;
a set of one or more wireless transceivers and a global positioning system (GPS) receiver,
wherein the GPS receiver is configured to:
receive a location of the lateral flow assay device from a plurality of satellites; and
send the location to the processor,
wherein the processor is configured to send the location of the lateral flow assay device to one or more electronic devices through the set of one or more wireless transceivers and one or more networks.

16. The lateral flow assay device of claim 1 further comprising:
a housing;
a disinfecting pad attached to the housing, the disinfecting pad comprising:
a quantity of disinfectant; and
a peelable cover configured to keep the disinfecting pad wet.

17. The lateral flow assay device of claim 1, wherein the tip is a first tip, the lateral flow assay device further comprising:
a buffer solution port comprising a cavity with a surface;
the buffer solution port configured to:
receive a quantity of buffer solution;
hold the buffer solution prior to a hole made in the cavity surface of the buffer solution port; and
apply the buffer solution to the capillary pad after the hole is made in the cavity surface of the buffer solution port;
wherein the breaker comprises a second tip, wherein the breaker is configured to:
press the second tip against the cavity surface of the buffer solution in response to receiving the force; and
in response to receiving the force, make a hole in the cavity surface of the buffer solution port with the second tip causing buffer solution held inside the buffer solution port to be applied to the capillary pad.

18. The lateral flow assay device of claim 17, wherein at least a portion of the cavity surface of the buffer solution port is made of a thin and breakable material, wherein the second tip makes the hole in the thin and breakable portion of the cavity surface of buffer solution port.

19. The lateral flow assay device of claim 17, wherein the cavity surface of the buffer solution port comprises a breakable tab, wherein the second tip makes the hole in the cavity surface of the buffer solution port by breaking the tab.

* * * * *